United States Patent
Malecha et al.

(10) Patent No.: US 9,903,831 B2
(45) Date of Patent: Feb. 27, 2018

(54) ACCURATE ANALYTE MEASUREMENTS FOR ELECTROCHEMICAL TEST STRIP BASED ON SENSED PHYSICAL CHARACTERISTIC(S) OF THE SAMPLE CONTAINING THE ANALYTE AND DERIVED BIOSENSOR PARAMETERS

(71) Applicant: LifeScan Scotland Limited, Inverness-shire (GB)

(72) Inventors: Michael Malecha, Muir of Ord (GB); Antony Smith, Inverness-shire (GB); David McColl, Inverness-shire (GB)

(73) Assignee: LifeScan Scotland Limited, Inverness (GB)

( * ) Notice: Subject to any disclaimer, the term of this patent is extended or adjusted under 35 U.S.C. 154(b) by 421 days.

(21) Appl. No.: 14/354,387

(22) PCT Filed: Dec. 28, 2012

(86) PCT No.: PCT/GB2012/053279
§ 371 (c)(1),
(2) Date: Apr. 25, 2014

(87) PCT Pub. No.: WO2013/098565
PCT Pub. Date: Jul. 4, 2013

(65) Prior Publication Data
US 2014/0284223 A1    Sep. 25, 2014

Related U.S. Application Data

(60) Provisional application No. 61/581,087, filed on Dec. 29, 2011, provisional application No. 61/581,089, (Continued)

(51) Int. Cl.
G06F 19/24     (2011.01)
G01N 27/26     (2006.01)
G01N 27/327    (2006.01)

(52) U.S. Cl.
CPC ......... *G01N 27/3274* (2013.01); *G01N 27/26* (2013.01); *G01N 27/3272* (2013.01); *G06F 19/24* (2013.01)

(58) Field of Classification Search
CPC .......... G01N 27/3274; G01N 27/3272; G01N 27/26; G06F 19/24
See application file for complete search history.

(56) References Cited

U.S. PATENT DOCUMENTS

| | | |
|---|---|---|
| 4,919,770 A | 4/1990 | Preidel et al. |
| 5,001,048 A | 3/1991 | Taylor et al. |

(Continued)

FOREIGN PATENT DOCUMENTS

| | | |
|---|---|---|
| AU | 738325 B2 | 9/2001 |
| CN | 1183384 C | 1/2005 |

(Continued)

OTHER PUBLICATIONS

First Office Action issued in corresponding Chinese Patent Application No. 201280070965.7, dated Oct. 10, 2015, 36 pages.

(Continued)

*Primary Examiner* — Luan V Van
*Assistant Examiner* — Steven E Rosenwald

(57) ABSTRACT

Various embodiments for a method that allow for a more accurate analyte concentration with a biosensor by determining at least one physical characteristic, typically hematocrit, of the sample containing the analyte and deriving from this characteristic a parameter relating to the biosensor to attain accurate glucose concentration.

20 Claims, 22 Drawing Sheets

Related U.S. Application Data filed on Dec. 29, 2011, provisional application No. 61/581,099, filed on Dec. 29, 2011, provisional application No. 61/581,100, filed on Dec. 29, 2011, provisional application No. 61/654,013, filed on May 31, 2012.

(56) References Cited

U.S. PATENT DOCUMENTS

| | | |
|---|---|---|
| 5,243,516 A | 9/1993 | White |
| 5,429,735 A | 7/1995 | Johnson et al. |
| 5,437,999 A | 8/1995 | Diebold et al. |
| 5,508,203 A | 4/1996 | Fuller et al. |
| 5,704,354 A | 1/1998 | Preidel et al. |
| 5,708,247 A | 1/1998 | McAleer et al. |
| 5,792,668 A | 8/1998 | Fuller et al. |
| 5,951,836 A | 9/1999 | McAleer et al. |
| 6,001,239 A | 12/1999 | Douglas et al. |
| 6,179,979 B1 | 1/2001 | Hodges et al. |
| 6,193,873 B1 | 2/2001 | Ohara et al. |
| 6,241,862 B1 | 6/2001 | McAleer et al. |
| 6,284,125 B1 | 9/2001 | Hodges et al. |
| 6,287,451 B1 | 9/2001 | Winarta et al. |
| 6,391,645 B1 | 5/2002 | Huang et al. |
| 6,413,410 B1 | 7/2002 | Hodges et al. |
| 6,475,372 B1 | 11/2002 | Ohara et al. |
| 6,517,482 B1 | 2/2003 | Elden et al. |
| 6,576,117 B1 | 6/2003 | Iketaki et al. |
| 6,645,368 B1 | 11/2003 | Beaty et al. |
| 6,685,633 B2 | 2/2004 | Albert et al. |
| 6,716,577 B1 | 4/2004 | Yu et al. |
| 6,733,655 B2 | 5/2004 | Davies et al. |
| 6,749,887 B1 | 6/2004 | Dick et al. |
| 6,767,441 B1* | 7/2004 | Cai .................. C12Q 1/004 |
| | | 204/403.03 |
| 6,841,389 B2 | 1/2005 | Novikov et al. |
| 6,863,801 B2 | 3/2005 | Hodges et al. |
| 6,890,421 B2 | 5/2005 | Ohara et al. |
| 7,018,843 B2 | 3/2006 | Heller |
| 7,045,046 B2 | 5/2006 | Chambers et al. |
| 7,050,847 B2 | 5/2006 | Ollmar et al. |
| 7,258,769 B2 | 8/2007 | Cui et al. |
| 7,291,256 B2 | 11/2007 | Teodorczyk et al. |
| 7,338,639 B2 | 3/2008 | Burke et al. |
| 7,390,667 B2 | 6/2008 | Burke et al. |
| 7,407,811 B2 | 8/2008 | Burke et al. |
| 7,452,457 B2 | 11/2008 | Burke et al. |
| 7,488,601 B2 | 2/2009 | Burke et al. |
| 7,494,816 B2 | 2/2009 | Burke et al. |
| 7,498,132 B2 | 3/2009 | Yu et al. |
| 7,597,793 B2 | 10/2009 | Burke et al. |
| 7,601,249 B2 | 10/2009 | Iyengar et al. |
| 7,604,721 B2 | 10/2009 | Groll et al. |
| 7,645,373 B2 | 1/2010 | Groll et al. |
| 7,645,421 B2 | 1/2010 | Groll |
| 7,678,250 B2 | 3/2010 | Bell et al. |
| 7,718,439 B2 | 5/2010 | Groll |
| 7,727,467 B2 | 6/2010 | Burke et al. |
| 7,749,437 B2 | 7/2010 | Mosoiu et al. |
| 7,751,864 B2 | 7/2010 | Buck, Jr. |
| 7,829,023 B2 | 11/2010 | Burke et al. |
| 7,879,618 B2 | 2/2011 | Mosoiu et al. |
| 7,892,849 B2 | 2/2011 | Burke et al. |
| 7,923,258 B2 | 4/2011 | Heller |
| 7,927,882 B2 | 4/2011 | Heller |
| 7,955,492 B2 | 6/2011 | Fujiwara et al. |
| 7,964,089 B2 | 6/2011 | Harding et al. |
| 7,972,851 B2 | 7/2011 | Wang et al. |
| 7,972,861 B2 | 7/2011 | Deng et al. |
| 8,080,153 B2 | 12/2011 | Feldman et al. |
| 8,083,925 B2 | 12/2011 | Feldman et al. |
| 8,088,271 B2 | 1/2012 | Fujiwara et al. |
| 8,148,164 B2 | 4/2012 | Diebold et al. |
| 8,409,424 B2 | 4/2013 | Chen et al. |
| 8,623,660 B2 | 1/2014 | Kraft et al. |
| 2004/0005716 A9 | 1/2004 | Beaty et al. |
| 2004/0079652 A1 | 4/2004 | Vreeke et al. |
| 2004/0157339 A1* | 8/2004 | Burke .............. G01N 27/3274 |
| | | 436/149 |
| 2004/0256248 A1 | 12/2004 | Burke et al. |
| 2007/0084734 A1 | 4/2007 | Roberts et al. |
| 2007/0087397 A1 | 4/2007 | Kraft et al. |
| 2008/0083618 A1 | 4/2008 | Neel et al. |
| 2008/0156662 A1 | 7/2008 | Wu et al. |
| 2008/0274447 A1 | 11/2008 | Mecklenburg |
| 2009/0177406 A1 | 7/2009 | Wu |
| 2009/0184004 A1 | 7/2009 | Chatelier et al. |
| 2009/0194432 A1 | 8/2009 | Deng |
| 2009/0223834 A1 | 9/2009 | Cai et al. |
| 2009/0236237 A1 | 9/2009 | Shinno et al. |
| 2009/0301899 A1 | 12/2009 | Hodges et al. |
| 2010/0005865 A1 | 1/2010 | Miura |
| 2010/0089775 A1 | 4/2010 | Chen et al. |
| 2010/0170807 A1 | 7/2010 | Diebold et al. |
| 2010/0206749 A1 | 8/2010 | Choi |
| 2010/0276303 A1 | 11/2010 | Fujiwara et al. |
| 2010/0283488 A1 | 11/2010 | Nakamura et al. |
| 2010/0320097 A1 | 12/2010 | Miyazaki et al. |
| 2011/0030093 A1 | 2/2011 | Dhugga |
| 2011/0036729 A1 | 2/2011 | Matsuda et al. |
| 2011/0168575 A1 | 7/2011 | Lica et al. |
| 2011/0294554 A1 | 12/2011 | Barratt et al. |
| 2011/0297554 A1 | 12/2011 | Wu et al. |
| 2011/0297557 A1 | 12/2011 | Wu et al. |
| 2011/0301857 A1 | 12/2011 | Huang et al. |
| 2012/0031777 A1 | 2/2012 | Burke et al. |
| 2012/0043227 A1 | 2/2012 | Miyazaki et al. |
| 2012/0129423 A1 | 5/2012 | Finizza |
| 2014/0209482 A1 | 7/2014 | Uchiyama |

FOREIGN PATENT DOCUMENTS

| | | |
|---|---|---|
| CN | 101517093 A | 8/2009 |
| EP | 749332 B1 | 3/1995 |
| EP | 691539 B1 | 6/1995 |
| EP | 1394545 A1 | 3/2004 |
| EP | 1828759 B1 | 10/2005 |
| EP | 1804048 B1 | 12/2005 |
| EP | 1042667 B1 | 6/2009 |
| EP | 2098857 A2 | 9/2009 |
| JP | 2001527215 A | 12/2001 |
| JP | 2003501627 A | 1/2003 |
| JP | 2007524826 A | 8/2007 |
| JP | 2009168815 A | 7/2009 |
| JP | 2009528540 A | 8/2009 |
| JP | 2009294213 A | 12/2009 |
| JP | 2010504524 A | 2/2010 |
| JP | 2011506966 A | 3/2011 |
| WO | WO 9932881 A1 | 7/1999 |
| WO | 03056345 A1 | 7/2003 |
| WO | WO 2006040200 A1 | 4/2006 |
| WO | WO 2006/070200 A1 | 7/2006 |
| WO | 2007100651 A1 | 9/2007 |
| WO | 2008036516 A1 | 3/2008 |
| WO | WO 2008/036516 A1 | 3/2008 |
| WO | WO 2008/040998 A2 | 4/2008 |
| WO | WO 2008/049075 A2 | 4/2008 |
| WO | 2009108239 A2 | 9/2009 |
| WO | WO 2010/049669 A1 | 5/2010 |
| WO | 2010061629 A1 | 6/2010 |
| WO | 2010110945 A1 | 9/2010 |
| WO | WO 2011/121292 A1 | 10/2011 |

OTHER PUBLICATIONS

U.S. Appl. No. 61/530,795, filed Sep. 2, 2011, McColl et al.
U.S. Appl. No. 61/530,808, filed Sep. 2, 2011, McColl et al.
U.S. Appl. No. 61/581,087, filed Dec. 29, 2011, Malecha et al.
U.S. Appl. No. 61/581,089, filed Dec. 29, 2011, Malecha et al.
U.S. Appl. No. 61/581,099, filed Dec. 29, 2011, Malecha et al.
U.S. Appl. No. 61/581,100, filed Dec. 29, 2011, Smith et al.
U.S. Appl. No. 61/654,013, filed May 31, 2012, Malecha et al.

(56) References Cited

OTHER PUBLICATIONS

International Application No. PCT/GB2012/053276, PCT International Search Report and Written Opinion, 13 pages, dated May 3, 2013.
International Application No. PCT/GB2012/053277, PCT International Search Report and Written Opinion, 13 pages, dated May 3, 2013.
International Application No. PCT/GB2012/053279, PCT International Search Report and Written Opinion, 13 pages, dated May 3, 2013.
Patent Examination Report issued in related Australian Patent Application No. 2012327229, dated May 28, 2014, 5 pages.
Wegener, Joachim et al., "Electric Cell-Substrate Impedance Sensing (ECIS) as a Noninvasive Means to Monitor the Kinetics of Cell Spreading to Artificial Surfaces,"Experimental Cell Research 259, 158-166 (2000) doi:10.1006/excr.2000.4919, available online at http://www.idealibrary.coml.
Kohma, Takuya et al., "Utilization of AC Impedance Measurements for Electrochemical Glucose Sensing Using Glucose Oxidase to Improve Detection Selectivity," Bull. Chem. Soc. Jpn. vol. 80, No. 1, 158-165 (2007).
Baskurt, Oguz K. et al., "Blood Rheology and Hemodynamics," Seminars in Thrombosis and Hemostasis, vol. 29, No. 5, 2003.
Nordbotten, Bernt, J. et al., "Methods for calculating phase angle from measured whole body bioimpedance modulus."
Wang, J. et al., "Electrochemical Impedance Biosensor for Glucose Detection Utilizing a Periplasmic E. coli Receptor Protein," Electrochemical and Solid-State Letters, 8 (8) H61-H64 (2005).
Caduff, A. et al., "First human experiments with a novel non-invasive, non-optical continuous glucose monitoring system," Biosensors and Bioelectronics 19 (2003) 209-217.
Guevara, Edgar et al., "Prediction of Glucose Concentration by Impedance Phase Measurements," CP1032, Medical Physics—Tenth Symposium of Medical Physics, 2008 American Institute of Physics 978-0-7354-0556, 259-261.
Park, J.-H. et al., "The correlation of the complex dielectric constant and blood glucose at low frequency," Biosensors and Bioelectronics 19 (2003) 321-324.
De Vries, P.M.J.M. et al., "Implications of the dielectrical behavior of human blood for continuous online measurement of haematocrit," Med. & Biol. Eng. & Comput. 1993, 31, 445-448.
"Annex A—Bioimpedance monitoring for physicians: an overview," pp. 131-178.
Koschinsky, T. et al., "Sensors for glucose monitoring: technical and clinical aspects," Diabetes Metab Res Rev 2001; 17: 113-123.
Marks, Vincent, "Blood glucose: its measurement and clinical importance," Clinica Chimica Acta 251 (1996) 3-17.
Shervedani, Reza Karimi et al., "A novel method for glucose determination based on electrochemical impedance spectroscopy using glucose oxidase self-assembled biosensor," Bioelectrochemistry 69 (2006) 201-208.
Tura, Andrea et al., "Non-invasive glucose monitoring: Assessment of technologies and devices according to quantitative criteria," Diabetes Research and Clinical Practice 77 (2007) 16-40.
Tierney, M.J. et al., "Clinical evaluation of the GlucoWatch® biographer: a continual, non-invasive glucose monitor for patients with diabetes," Biosensors & Bioelectronics 16 (2001) 621-629.
Tura, A. et al., "Impedance spectroscopy of solutions at physiological glucose concentrations," Biophysical Chemistry 129 (2007) 235-241.
International Preliminary Report on Patentability issued in related International Patent Application No. PCT/GB2012/053279, dated Jul. 1, 2004, 10 pages.
Patent Examination Report issued in related Australian Patent Application No. 2012340500, dated Aug. 4, 2014, 3 pages.
International Preliminary Report on Patentability issued in related International Patent Application No. PCT/GB2012/053277, dated Jul. 1, 2004, 11 pages.
International Preliminary Report on Patentability issued in related International Patent Application No. PCT/GB2012/053276, dated Jul. 1, 2004, 11 pages.
Notice of Reasons for Rejection issued in related Japanese Patent Application No. 2014-549536, dated Oct. 4, 2016, 11 pages.
Examination Report issued in related Taiwan Patent Application No. 101151342, dated Sep. 26, 2016, 11 pages.
European Search Report issued in related European Patent Application No. 16189773, dated Mar. 17, 2017, 12 pages.

* cited by examiner

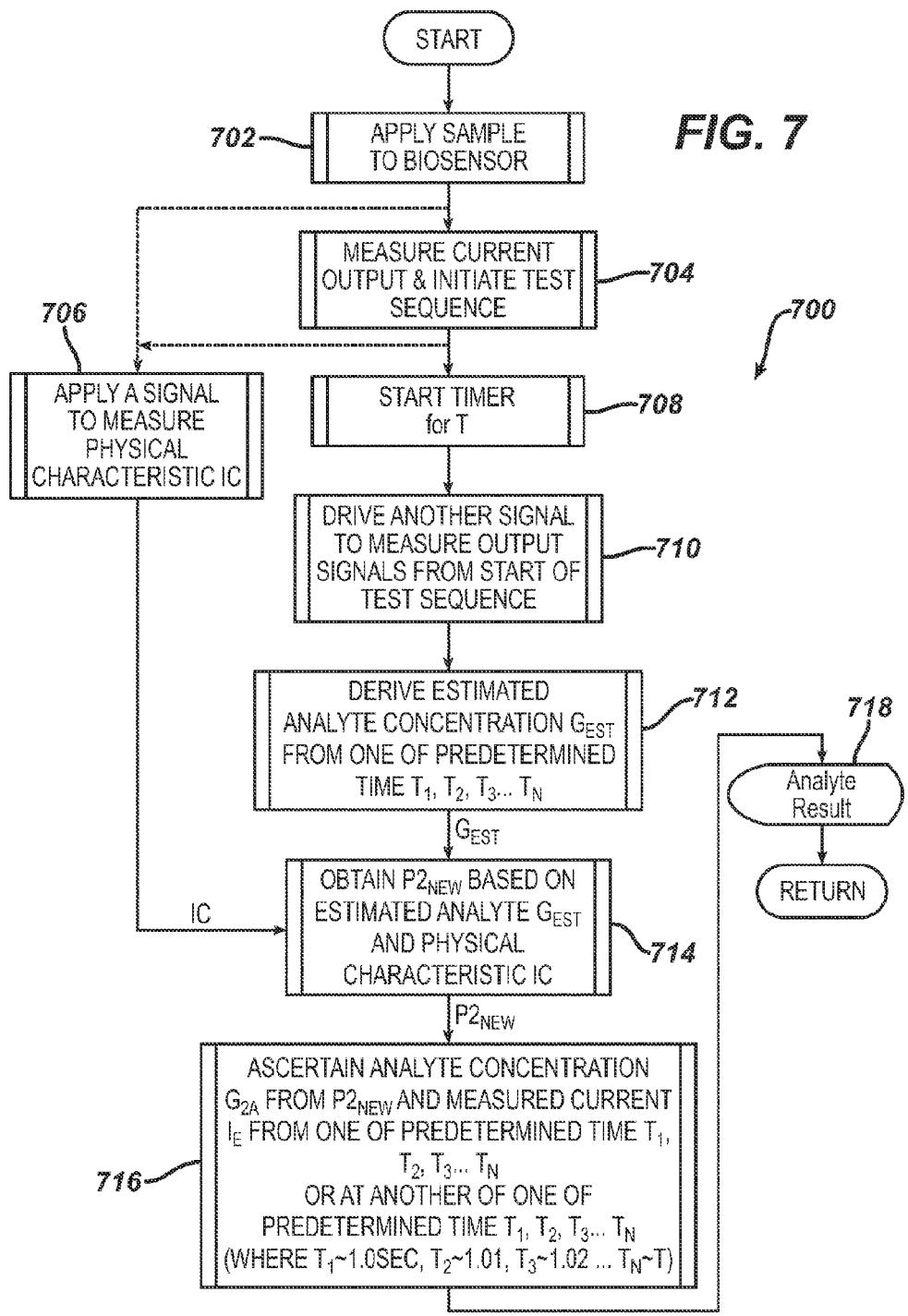

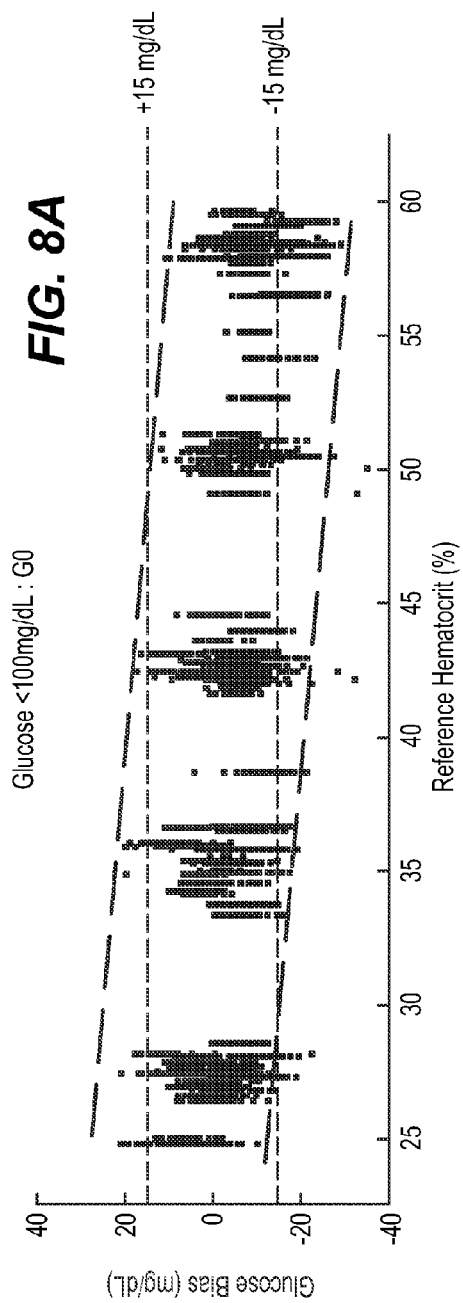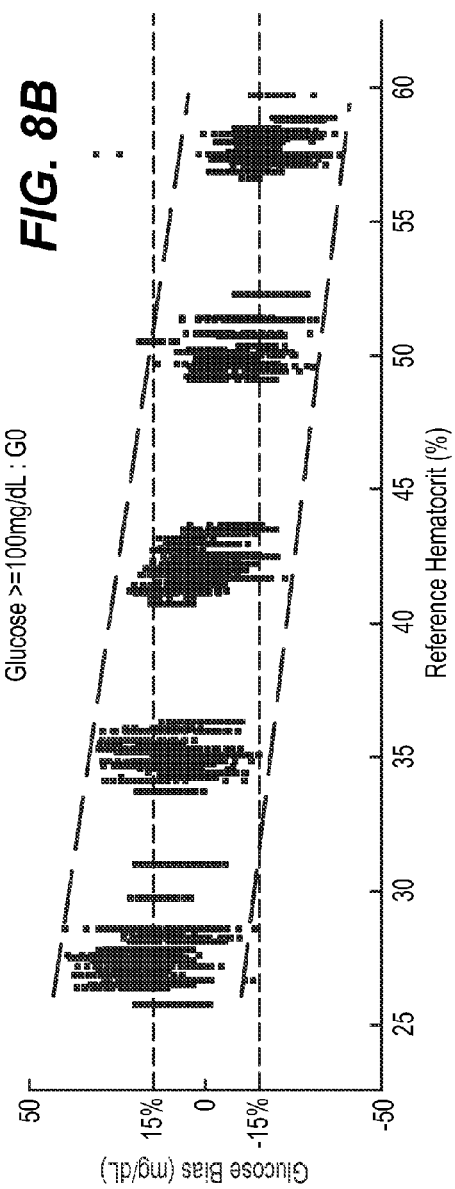

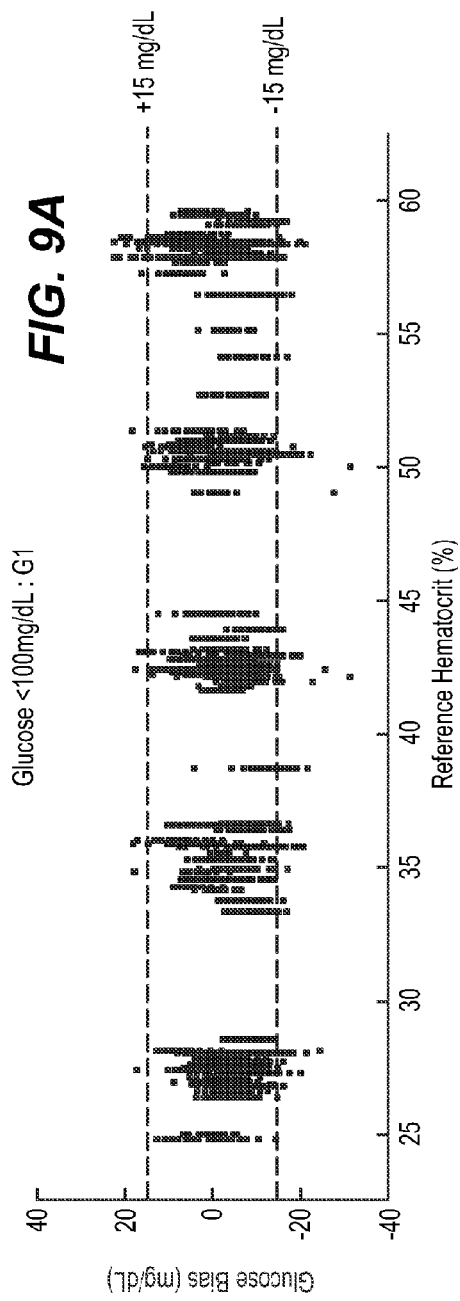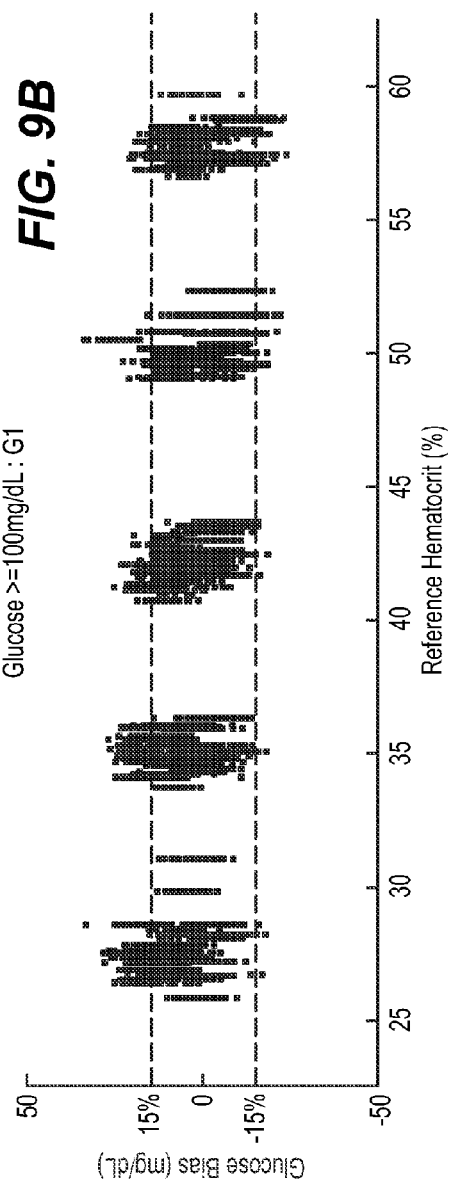

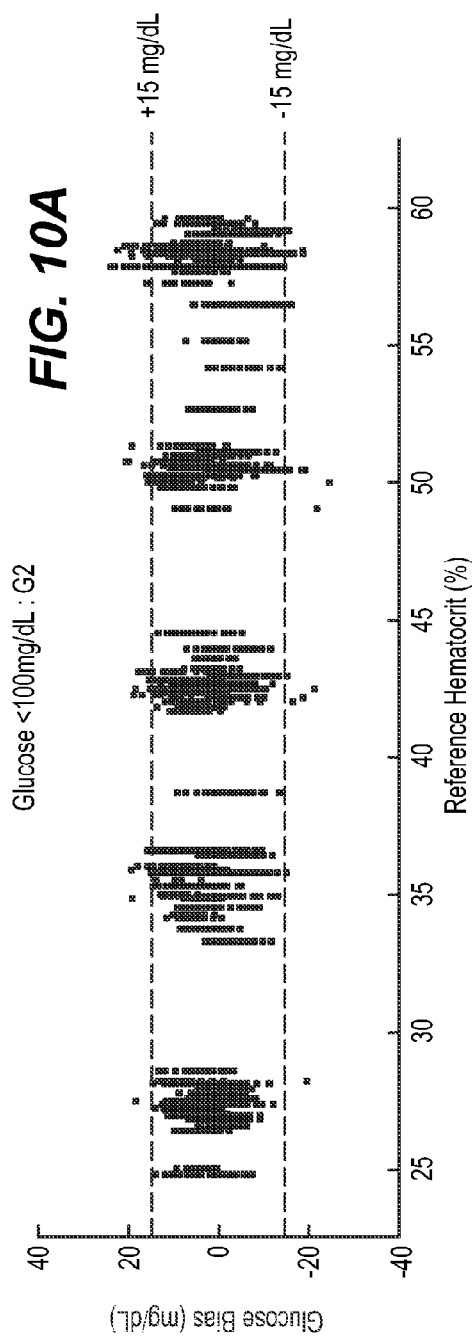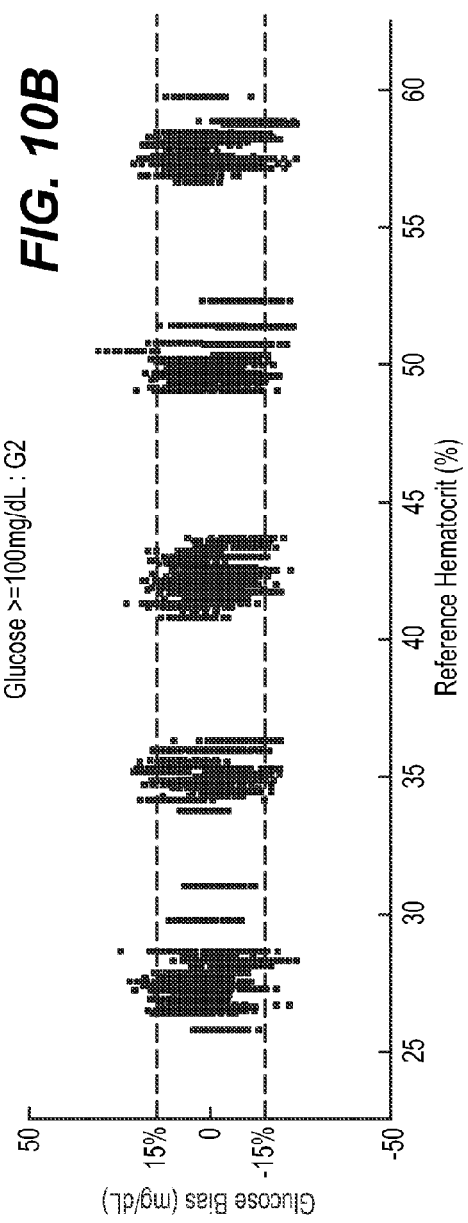

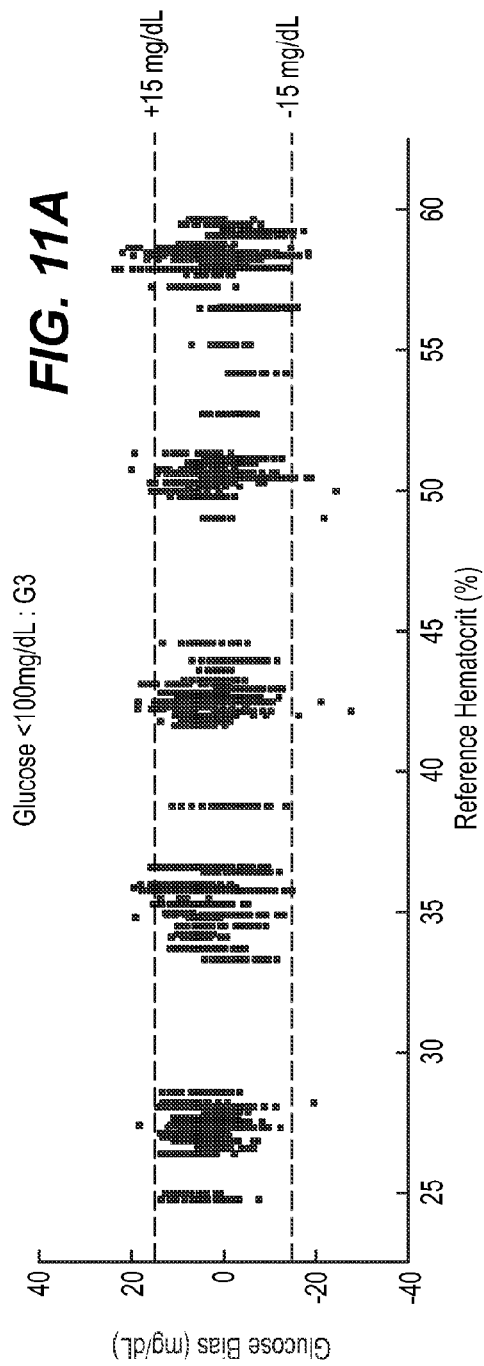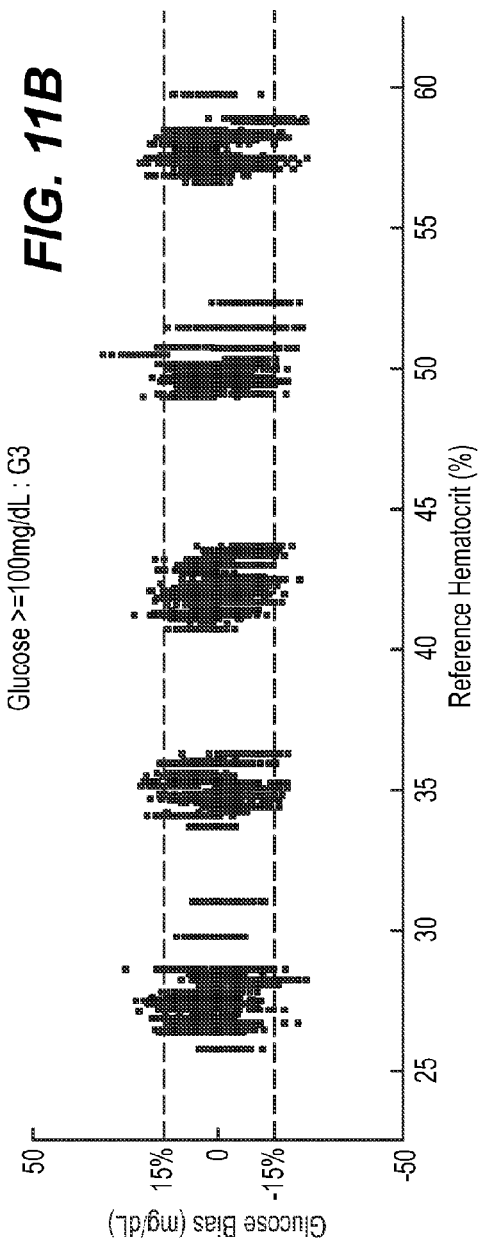
FIG. 11A
FIG. 11B

ACCURATE ANALYTE MEASUREMENTS FOR ELECTROCHEMICAL TEST STRIP BASED ON SENSED PHYSICAL CHARACTERISTIC(S) OF THE SAMPLE CONTAINING THE ANALYTE AND DERIVED BIOSENSOR PARAMETERS

PRIORITY

This National Stage application of International Application PCT/GB2012/053279 filed on Dec. 28, 2012 claims the benefits of priority of prior filed U.S. Provisional Patent Application Ser. Nos. 61/581,087; 61/581,089; 61/581,099; and 61/581,100, all filed on the same day of Dec. 29, 2011, U.S. Provisional Patent Application Ser. No. 61/654,013, filed on 31 May 2012, International Patent Application Nos. PCT/GB2012/053276 and PCT/GB2012/053277, both filed on 28 Dec. 2012, and all the prior applications ("Priority Applications") are hereby incorporated by reference as if fully set forth herein.

BACKGROUND

Electrochemical glucose test strips, such as those used in the OneTouch® Ultra®whole blood testing kit, which is available from LifeScan, Inc., are designed to measure the concentration of glucose in a physiological fluid sample from patients with diabetes. The measurement of glucose can be based on the selective oxidation of glucose by the enzyme glucose oxidase (GO). The reactions that can occur in a glucose test strip are summarized below in Equations 1 and 2.

$$\text{Glucose} + GO_{(ox)} \rightarrow \text{Gluconic Acid} + GO_{(red)} \quad \text{Eq. 1}$$

$$GO_{(red)} + 2Fe(CN)_6^{3-} \rightarrow GO_{(ox)} + 2Fe(CN)_6^{4-} \quad \text{Eq. 2}$$

As illustrated in Equation 1, glucose is oxidized to gluconic acid by the oxidized form of glucose oxidase ($GO_{(ox)}$). It should be noted that $GO_{(ox)}$ may also be referred to as an "oxidized enzyme." During the reaction in Equation 1, the oxidized enzyme $GO_{(ox)}$ is converted to its reduced state, which is denoted as $GO_{(red)}$ (i.e., "reduced enzyme"). Next, the reduced enzyme $GO_{(red)}$ is re-oxidized back to $GO_{(ox)}$ by reaction with $Fe(CN)_6^{3-}$ the oxidized (referred to as either oxidized mediator or ferricyanide) as illustrated in Equation 2. During the re-generation of $GO_{(red)}$ back to its oxidized state $GO_{(ox)}$, $Fe(CN)_6^{3-}$ is reduced to $Fe(CN)_6^{4-}$ (referred to as either reduced mediator or ferrocyanide).

When the reactions set forth above are conducted with a test signal in the form of potential applied between two electrodes, a test signal in the form of a current can be created by the electrochemical re-oxidation of the reduced mediator at the electrode surface. Thus, since, in an ideal environment, the amount of ferrocyanide created during the chemical reaction described above is directly proportional to the amount of glucose in the sample positioned between the electrodes, the test output signal generated would be proportional to the glucose content of the sample. A mediator, such as ferricyanide, is a compound that accepts electrons from an enzyme such as glucose oxidase and then donates the electrons to an electrode. As the concentration of glucose in the sample increases, the amount of reduced mediator formed also increases; hence, there is a direct relationship between the test output signal, resulting from the re-oxidation of reduced mediator, and glucose concentration. In particular, the transfer of electrons across the electrical interface results in the flow of a test output signal (2 moles of electrons for every mole of glucose that is oxidized). The test output signal resulting from the introduction of glucose can, therefore, be referred to as a glucose output signal.

Electrochemical biosensors may be adversely affected by the presence of certain blood components that may undesirably affect the measurement and lead to inaccuracies in the detected signal. This inaccuracy may result in an inaccurate glucose reading, leaving the patient unaware of a potentially dangerous blood sugar level, for example. As one example, the blood hematocrit level (i.e. the percentage of the amount of blood that is occupied by red blood cells) can erroneously affect a resulting analyte concentration measurement.

Variations in a volume of red blood cells within blood can cause variations in glucose readings measured with disposable electrochemical test strips. Typically, a negative bias (i.e., lower calculated analyte concentration) is observed at high hematocrit, while a positive bias (i.e., higher calculated analyte concentration) is observed at low hematocrit. At high hematocrit, for example, the red blood cells may impede the reaction of enzymes and electrochemical mediators, reduce the rate of chemistry dissolution since there is less plasma volume to solvate the chemical reactants, and slow diffusion of the mediator. These factors can result in a lower than expected glucose reading as less current is produced during the electrochemical process. Conversely, at low hematocrit, fewer red blood cells may affect the electrochemical reaction than expected, and a higher measured output signal can result. In addition, the physiological fluid sample resistance is also hematocrit dependent, which can affect voltage and/or current measurements.

Several strategies have been used to reduce or avoid hematocrit based variations on blood glucose. For example, test strips have been designed to incorporate meshes to remove red blood cells from the samples, or have included various compounds or formulations designed to increase the viscosity of red blood cells and attenuate the effect of low hematocrit on concentration determinations. Other test strips have included lysis agents and systems configured to determine hemoglobin concentration in an attempt to correct hematocrit. Further, biosensors have been configured to measure hematocrit by measuring an electrical response of the fluid sample via alternating signals or a change in optical variations after irradiating the physiological fluid sample with light, or measuring hematocrit based on a function of sample chamber fill time. These sensors have certain disadvantages. A common technique of the strategies involving detection of hematocrit is to use the measured hematocrit value to correct or change the measured analyte concentration, which technique is generally shown and described in the following respective US Patent Application Publication Nos. 2010/0283488; 2010/0206749; 2009/0236237; 2010/0276303; 2010/0206749; 2009/0223834; 2008/0083618; 2004/0079652; 2010/0283488; 2010/0206749; 2009/0194432; or U.S. Pat. Nos. 7,972,861 and 7,258,769, all of which are incorporated by reference herein to this application.

SUMMARY OF THE DISCLOSURE

Applicants have provided various embodiments of a technique to allow for improved glucose measurement using a relationship between batch slope and physical characteristic (e.g., hematocrit) to derive a new batch slope that can be used to determine the analyte concentration based on this derived batch slope of an electrochemical biosensor. Advantageously, this new technique does not rely on correction(s)

or modification(s) to be made to an analyte measurement, thereby reducing test time while at the same time improving accuracy.

In a first aspect of applicants' disclosure, a method is provided that allows users to obtain results of analyte concentrations with greater accuracy. The method can be achieved by: applying a signal to the sample to determine a physical characteristic of the sample; driving another signal to the sample to cause a physical transformation of the sample; measuring at least one output signal from the sample; obtaining an estimated analyte concentration from the at least one output signal at one of a plurality of predetermined time positions from the start of the test sequence and at least one predetermined parameter of the biosensor; generating a first parametric factor of the biosensor based on the physical characteristic of the sample; calculating a first analyte concentration based on the first parametric factor of the biosensor and at least one output signal measured at one of the plurality of predetermined time positions from the start of the test sequence; generating a second parametric factor of the biosensor based on the estimated analyte concentration and the physical characteristic of the sample; calculating a second analyte concentration based on the second parametric factor of the biosensor and at least one output signal measured at one of the plurality of predetermined time positions from the start of the test sequence; generating a third parametric factor of the biosensor based on the first analyte concentration and the physical characteristic; calculating a third analyte concentration based on the third parametric factor of the biosensor and at least one output signal measured at one of the plurality of predetermined time positions from the start of the test sequence; and annunciating at least one of the first, second, and third analyte concentrations.

In yet another aspect, a method is provided that allows users to obtain results of analyte concentrations with greater accuracy. The method can be achieved by: starting an analyte test sequence upon deposition of a sample; applying a signal to the sample to determine a physical characteristic of the sample; driving another signal to the sample to cause a physical transformation of the sample; measuring at least one output signal from the sample; deriving an estimated analyte concentration from the at least one output signal measured at one of a plurality of predetermined time positions from the start of the test sequence; obtaining a new parameter of the biosensor based on the estimated analyte concentration and the physical characteristic of the sample; calculating an analyte concentration based on the new parameter of the biosensor and a output signal measured at the one or another of the plurality of predetermined time positions from the start of the test sequence; and annunciating the analyte concentration.

In yet a further aspect of the disclosure, a method is provided that allows users to obtain results of analyte concentrations with greater accuracy. The method can be achieved by: starting an analyte test sequence upon deposition of a sample on the biosensor; applying a signal to the sample to determine a physical characteristic of the sample; driving another signal to the sample to cause a physical transformation of the sample; measuring at least one output signal from the sample; generating a first new batch parameter of the biosensor based on the physical characteristic of the sample; calculating a first analyte concentration based on the first new batch parameter of the biosensor and an output signal measured at one of a plurality of predetermined time positions from the start of the test sequence; and annunciating the first analyte concentration.

In the aforementioned aspects of the disclosure, the steps of determining, estimating, calculating, computing, deriving and/or utilizing (possibly in conjunction with an equation) may be performed be an electronic circuit or a processor. These steps may also be implemented as executable instructions stored on a computer readable medium; the instructions, when executed by a computer may perform the steps of any one of the aforementioned methods.

In additional aspects of the disclosure, there are computer readable media, each medium comprising executable instructions, which, when executed by a computer, perform the steps of any one of the aforementioned methods.

In additional aspects of the disclosure, there are devices, such as test meters or analyte testing devices, each device or meter comprising an electronic circuit or processor configured to perform the steps of any one of the aforementioned methods.

These and other embodiments, features and advantages will become apparent to those skilled in the art when taken with reference to the following more detailed description of the exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements), in which:

FIG. 3B illustrates a variation of the test strip of FIG. 3A in which one physical characteristic sensing electrode is disposed proximate the entrance and the other physical characteristic sensing electrode is at the terminal end of the test cell with the measurement electrodes disposed between the pair of physical characteristic sensing electrodes.

FIGS. 3C and 3D illustrate variations of FIG. 3A or 3B in which the physical characteristic sensing electrodes are disposed next to each other at the terminal end of the test chamber with the measurement electrodes upstream of the physical characteristic sensing electrodes.

FIG. 7 illustrates an alternative fourth technique in which FIG. 7 is a template for which any of the techniques in FIG. 6 can be utilized.

FIGS. 8A and 8B illustrate the accuracy of the various lots of biosensor used for Table 5 in the known technique.

FIGS. 9A and 9B illustrate the improvement in the accuracy of the various lots of biosensor in Table 5 for the first novel technique.

FIGS. 10A and 10B illustrate the improvement in the accuracy of the various lots of biosensor used in Table 5 for the second novel technique.

FIGS. 11A and 11B illustrate the improvement in the accuracy of the various lots of biosensor used in Table 5 for the third novel technique.

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment. As used herein, "oscillating signal" includes voltage signal(s) or current signal(s) that, respectively, change polarity or alternate direction of current or are multi-directional. Also used herein, the phrase "electrical signal" or "signal" is intended to include direct current signal, alternating signal or any signal within the electromagnetic spectrum. The terms "processor"; "microprocessor"; or "microcontroller" are intended to have the same meaning and are intended to be used interchangeably. As used herein, the term "annunciated" and variations on its root term indicate that an announcement may be provided via text, audio, visual or a combination of all modes or mediums of communication to a user. To inform the user of the qualitative aspect of the result, an indicia can be provided to indicate whether the result is outside of the desired range via a red indicia (or flashing message) or in-range by way of a green indicia or the like.

Figure 1:
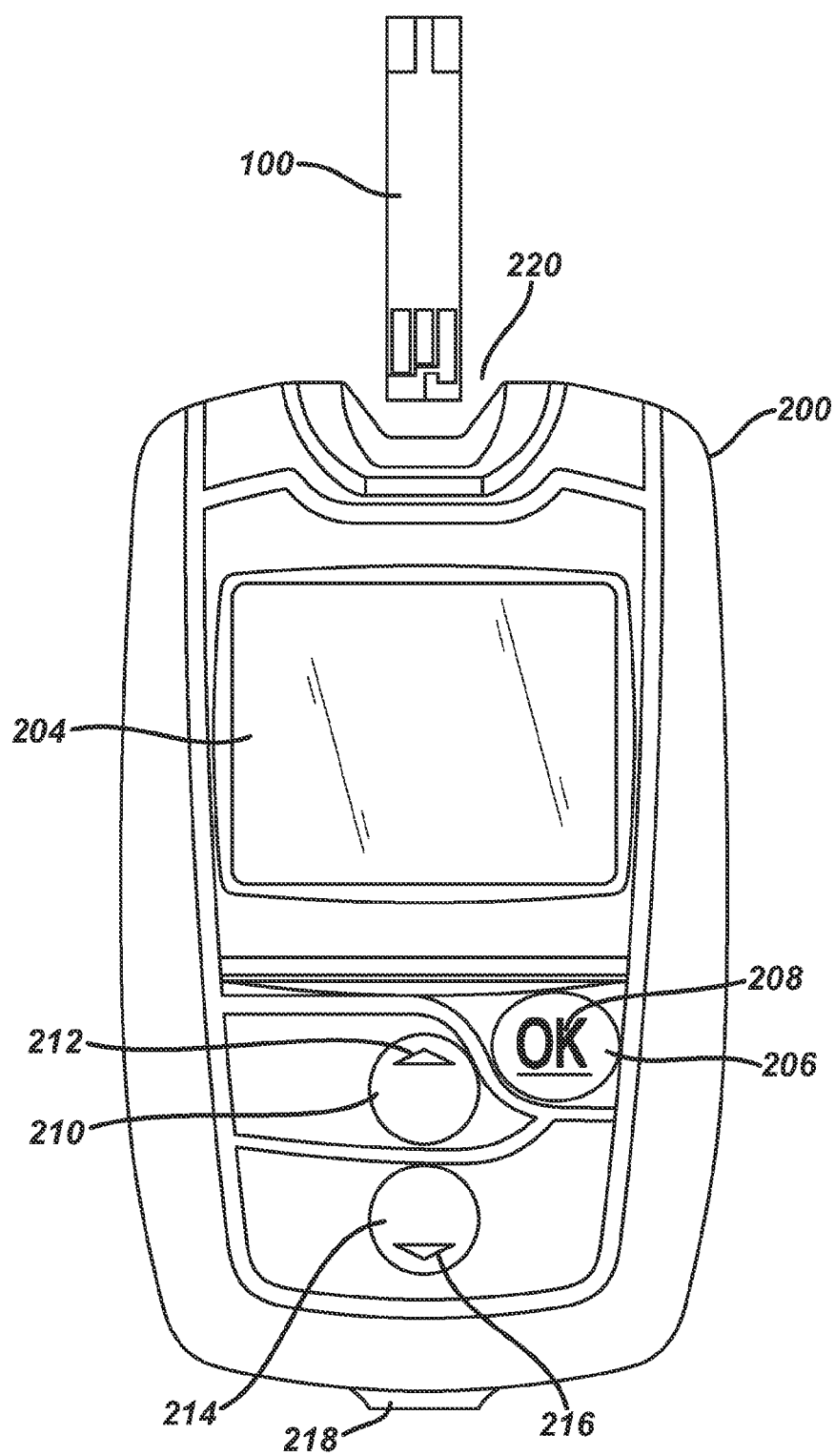
FIG. 1 illustrates an analyte measurement system.

FIG. 1 illustrates a test meter 200, for testing analyte (e.g., glucose) levels in the blood of an individual with a test strip produced by the methods and techniques illustrated and described herein. Test meter 200 may include user interface inputs (206, 210, 214), which can be in the form of buttons, for entry of data, navigation of menus, and execution of commands. Data can include values representative of analyte concentration, and/or information that are related to the everyday lifestyle of an individual. Information, which is related to the everyday lifestyle, can include food intake, medication use, the occurrence of health check-ups, general health condition and exercise levels of an individual. Test meter 200 can also include a display 204 that can be used to report measured glucose levels, and to facilitate entry of lifestyle related information.

Test meter 200 may include a first user interface input 206, a second user interface input 210, and a third user interface input 214. User interface inputs 206, 210, and 214 facilitate entry and analysis of data stored in the testing device, enabling a user to navigate through the user interface displayed on display 204. User interface inputs 206, 210, and 214 include a first marking 208, a second marking 212, and a third marking 216, which help in correlating user interface inputs to characters on display 204.

Test meter 200 can be turned on by inserting a test strip 100 (or its variants in the Priority Applications) into a strip port connector 220, by pressing and briefly holding first user interface input 206, or by the detection of data traffic across a data port 218. Test meter 200 can be switched off by removing test strip 100 (or its variants in the Priority Applications), pressing and briefly holding first user interface input 206, navigating to and selecting a meter off option from a main menu screen, or by not pressing any buttons for a predetermined time. Display 104 can optionally include a backlight.

In one embodiment, test meter 200 can be configured to not receive a calibration input for example, from any external source, when switching from a first test strip batch to a second test strip batch. Thus, in one exemplary embodiment, the meter is configured to not receive a calibration input from external sources, such as a user interface (such as inputs 206, 210, 214), an inserted test strip, a separate code key or a code strip, data port 218. Such a calibration input is not necessary when all of the test strip batches have a substantially uniform calibration characteristic. The calibration input can be a set of values ascribed to a particular test strip batch. For example, the calibration input can include a batch slope and a batch intercept value for a particular test strip batch. The calibrations input, such as batch slope and intercept values, may be preset within the meter as will be described below.

Figure 2A:
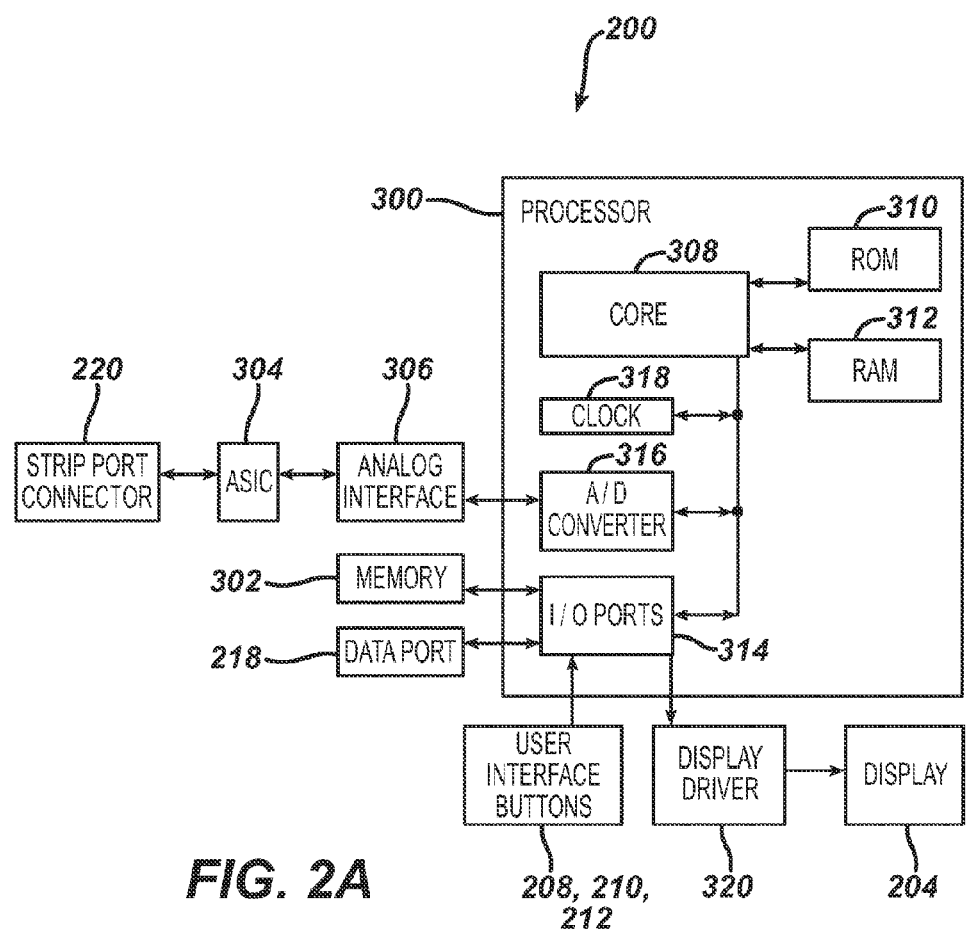
FIG. 2A illustrates in simplified schematic form the components of the meter 200.

Referring to FIG. 2A, an exemplary internal layout of test meter 200 is shown. Test meter 200 may include a processor 300, which in some embodiments described and illustrated herein is a 32-bit RISC microcontroller. In the preferred embodiments described and illustrated herein, processor 300 is preferably selected from the MSP 430 family of ultra-low power microcontrollers manufactured by Texas Instruments of Dallas, Tex. The processor can be bi-directionally connected via I/O ports 314 to a memory 302, which in some embodiments described and illustrated herein is an EEPROM. Also connected to processor 300 via I/O ports 214 are the data port 218, the user interface inputs 206, 210, and 214, and a display driver 320. Data port 218 can be connected to processor 300, thereby enabling transfer of data between memory 302 and an external device, such as a personal computer. User interface inputs 206, 210, and 214 are directly connected to processor 300. Processor 300 controls display 204 via display driver 320. Memory 302 may be pre-loaded with calibration information, such as batch slope and batch intercept values, during production of test meter 200. This pre-loaded calibration information can be accessed and used by processor 300 upon receiving a suitable signal (such as current) from the strip via strip port connector 220 so as to calculate a corresponding analyte level (such as blood glucose concentration) using the signal and the calibration information without receiving calibration input from any external source.

In embodiments described and illustrated herein, test meter 200 may include an Application Specific Integrated Circuit (ASIC) 304, so as to provide electronic circuitry used in measurements of glucose level in blood that has been applied to a test strip 100 (or its variants in the Priority Applications) inserted into strip port connector 220. Analog voltages can pass to and from ASIC 304 by way of an analog interface 306. Analog signals from analog interface 306 can be converted to digital signals by an A/D converter 316. Processor 300 further includes a core 308, a ROM 310 (containing computer code), a RAM 312, and a clock 318. In one embodiment, the processor 300 is configured (or programmed) to disable all of the user interface inputs except for a single input upon a display of an analyte value by the display unit such as, for example, during a time period after an analyte measurement. In an alternative embodiment, the processor 300 is configured (or programmed) to ignore any input from all of the user interface inputs except for a single input upon a display of an analyte value by the display unit. Detailed descriptions and illustrations of the meter 200 are shown and described in International Patent Application Publication No. WO2006040200, which is hereby incorporated by reference into this application as if fully set forth herein.

Figure 3A:
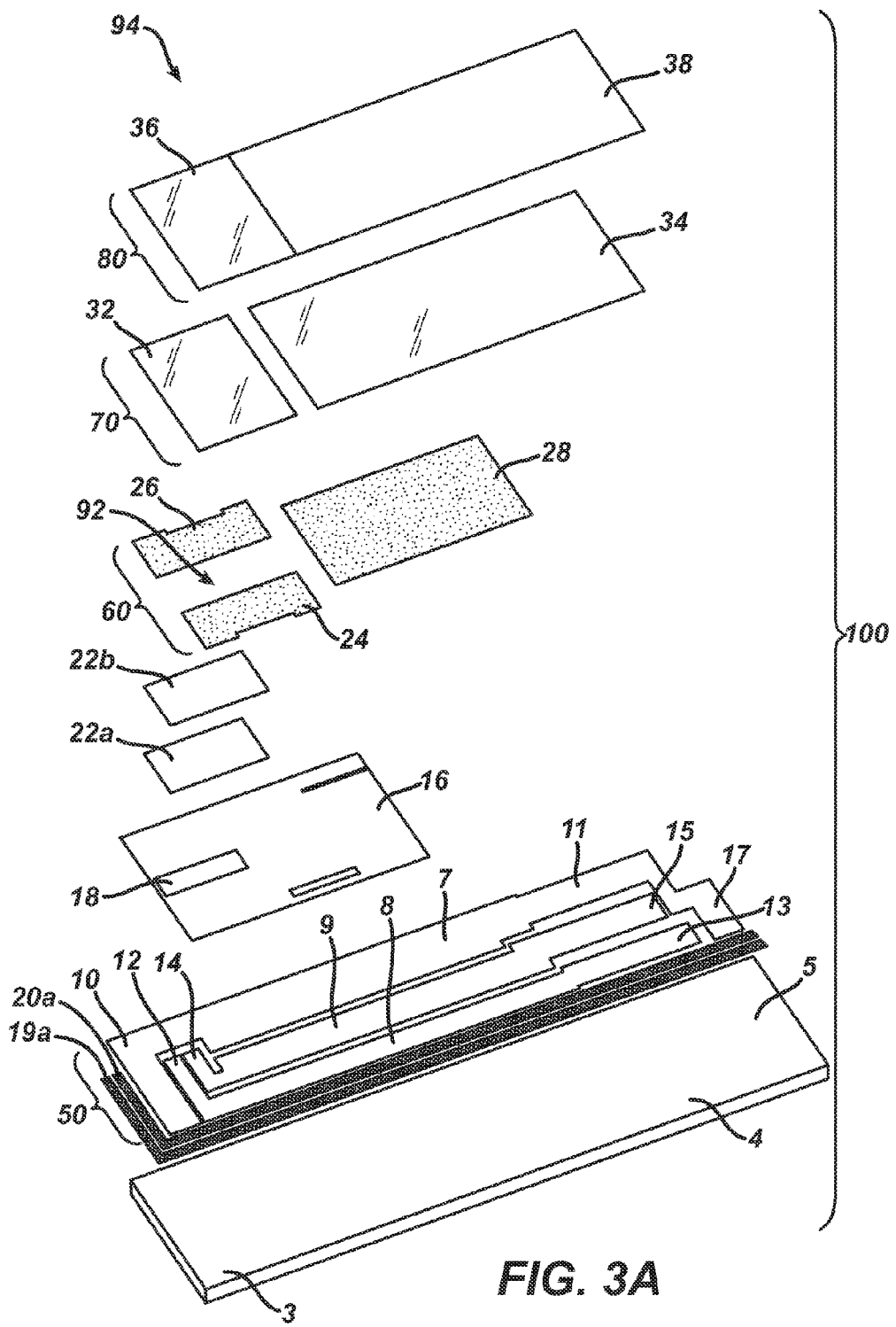
FIG. 3A illustrates the test strip 100 of the system of FIG. 1 in which there are two physical characteristic sensing electrodes upstream of the measurement electrodes.

FIG. 3A is an exemplary exploded perspective view of a test strip 100, which may include seven layers disposed on a substrate 5. The seven layers disposed on substrate 5 can be a first conductive layer 50 (which can also be referred to as electrode layer 50), an insulation layer 16, two overlapping reagent layers 22a and 22b, an adhesive layer 60 which includes adhesive portions 24, 26, and 28, a hydrophilic layer 70, and a top layer 80 which forms a cover 94 for the test strip 100. Test strip 100 may be manufactured in a series of steps where the conductive layer 50, insulation layer 16, reagent layers 22, and adhesive layer 60 are sequentially deposited on substrate 5 using, for example, a screen-printing process. Note that the electrodes 10, 12, and 14) are disposed for contact with the reagent layer 22a and 22b whereas the physical characteristic sensing electrodes 19a and 20a are spaced apart and not in contact with the reagent layer 22. Hydrophilic layer 70 and top layer 80 can be disposed from a roll stock and laminated onto substrate 5 as either an integrated laminate or as separate layers. Test strip 100 has a distal portion 3 and a proximal portion 4 as shown in FIG. 3A.

Figure 3B:
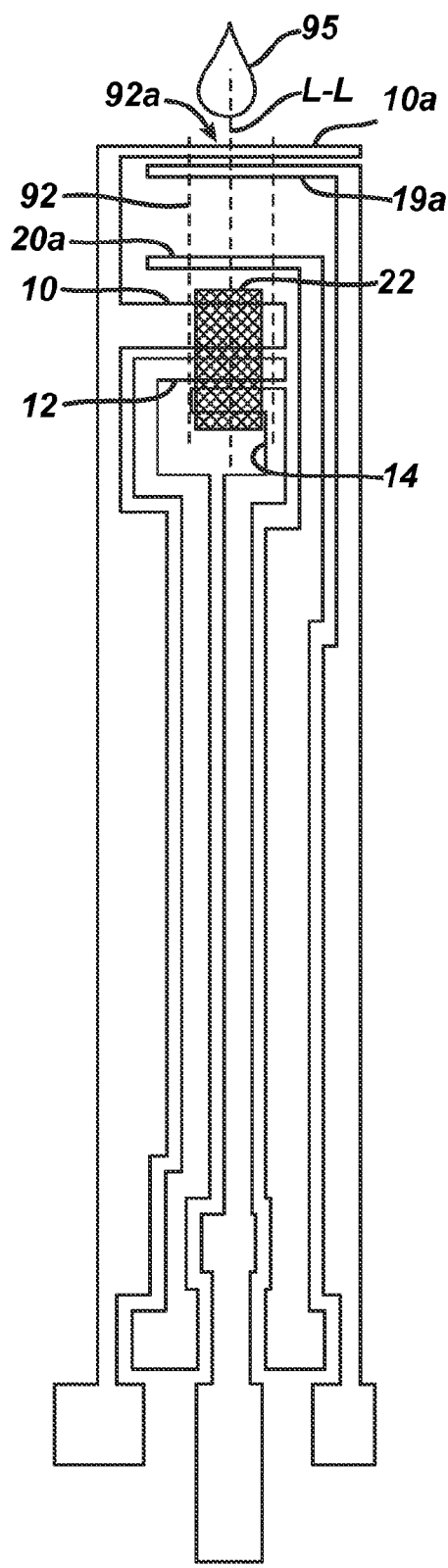
FIG. 3B illustrates a variation of the test strip of FIG. 3A in which a shielding or grounding electrode is provided for proximate the entrance of the test chamber.

Test strip 100 may include a sample-receiving chamber 92 through which a physiological fluid sample 95 may be drawn through or deposited (FIG. 3B). The physiological fluid sample discussed herein may be blood. Sample-receiving chamber 92 can include an inlet at a proximal end and an outlet at the side edges of test strip 100, as illustrated in FIG. 3A. A fluid sample 95 can be applied to the inlet along axis L-L (FIG. 3B) to fill a sample-receiving chamber 92 so that glucose can be measured. The side edges of a first adhesive pad 24 and a second adhesive pad 26 located adjacent to reagent layer 22 each define a wall of sample-receiving chamber 92, as illustrated in FIG. 3A. A bottom portion or "floor" of sample-receiving chamber 92 may include a portion of substrate 5, conductive layer 50, and insulation layer 16, as illustrated in FIG. 3A. A top portion or "roof" of sample-receiving chamber 92 may include distal hydrophilic portion 32, as illustrated in FIG. 3A. For test strip 100, as illustrated in FIG. 3A, substrate 5 can be used as a foundation for helping support subsequently applied layers. Substrate 5 can be in the form of a polyester sheet such as a polyethylene tetraphthalate (PET) material (Hostaphan PET supplied by Mitsubishi). Substrate 5 can be in a roll format, nominally 350 microns thick by 370 millimeters wide and approximately 60 meters in length.

A conductive layer is required for forming electrodes that can be used for the electrochemical measurement of glucose. First conductive layer 50 can be made from a carbon ink that is screen-printed onto substrate 5. In a screen-printing process, carbon ink is loaded onto a screen and then transferred through the screen using a squeegee. The printed carbon ink can be dried using hot air at about 140° C. The carbon ink can include VAGH resin, carbon black, graphite (KS15), and one or more solvents for the resin, carbon and graphite mixture. More particularly, the carbon ink may incorporate a ratio of carbon black:VAGH resin of about 2.90:1 and a ratio of graphite:carbon black of about 2.62:1 in the carbon ink.

For test strip 100, as illustrated in FIG. 3A, first conductive layer 50 may include a reference electrode 10, a first working electrode 12, a second working electrode 14, third and fourth physical characteristic sensing electrodes 19a and 19b, a first contact pad 13, a second contact pad 15, a reference contact pad 11, a first working electrode track 8, a second working electrode track 9, a reference electrode track 7, and a strip detection bar 17. The physical characteristic sensing electrodes 19a and 20a are provided with respective electrode tracks 19b and 20b. The conductive layer may be formed from carbon ink. First contact pad 13, second contact pad 15, and reference contact pad 11 may be adapted to electrically connect to a test meter. First working electrode track 8 provides an electrically continuous pathway from first working electrode 12 to first contact pad 13. Similarly, second working electrode track 9 provides an electrically continuous pathway from second working electrode 14 to second contact pad 15. Similarly, reference electrode track 7 provides an electrically continuous pathway from reference electrode 10 to reference contact pad 11. Strip detection bar 17 is electrically connected to reference contact pad 11. Third and fourth electrode tracks 19b and 20b connect to the respective electrodes 19a and 20a. A test meter can detect that test strip 100 has been properly inserted by measuring a continuity between reference contact pad 11 and strip detection bar 17, as illustrated in FIG. 3A.

Variations of the test strip 100 (FIG. 3A, 3B, 3c, or 3D) are shown of applicants' priority application Ser. Nos. 61/581,087; 61/581,089; 61/581,099; and 61/581,100, all filed on the same day of Dec. 29, 2011, and U.S. Provisional Patent Application Ser. No. 61/654,013, filed on 31 May 2012. It is the intention of applicants that the scope of the invention claimed herein is also applicable to the variety of strips described in these prior filed applications.

In the embodiment of FIG. 3B which is a variation of the test strip of FIG. 3A, an additional electrode 10a is provided as an extension of any of the plurality of electrodes 19a, 20a, 14, 12, and 10. It must be noted that the built-in shielding or grounding electrode 10a is used to reduce or eliminate any capacitance coupling between the finger or body of the user and the characteristic measurement electrodes 19a and 20a. The grounding electrode 10a allows for any capacitance to be directed away from the sensing electrodes 19a and 20a. To do this, the grounding electrode 10a can be connected any one of the other five electrodes or to its own separate contact pad (and track) for connection to ground on the meter instead of one or more of contact pads 15, 17, 13 via respective tracks 7, 8, and 9. In a preferred embodiment, the grounding electrode 10a is connected to one of the three electrodes that has reagent 22 disposed thereon. In a most preferred embodiment, the grounding electrode 10a is connected to electrode 10. Being the grounding electrode, it is advantageous to connect the grounding electrode to the reference electrode (10) so not to contribute any additional current to the working electrode measurements which may come from background interfering compounds in the sample. Further by connecting the shield or grounding electrode 10a to electrode 10 this is believed to effectively increase the size of the counter electrode 10 which can become limiting especially at high signals. In the embodiment of FIG. 3B, the reagent is arranged so that they are not in contact with the measurement electrodes 19a and 20a. Alternatively, in the embodiment of FIG. 3C, the reagent 22 is arranged so that the reagent 22 contacts at least one of the sensing electrodes 19a and 20a.

Figure 3C:
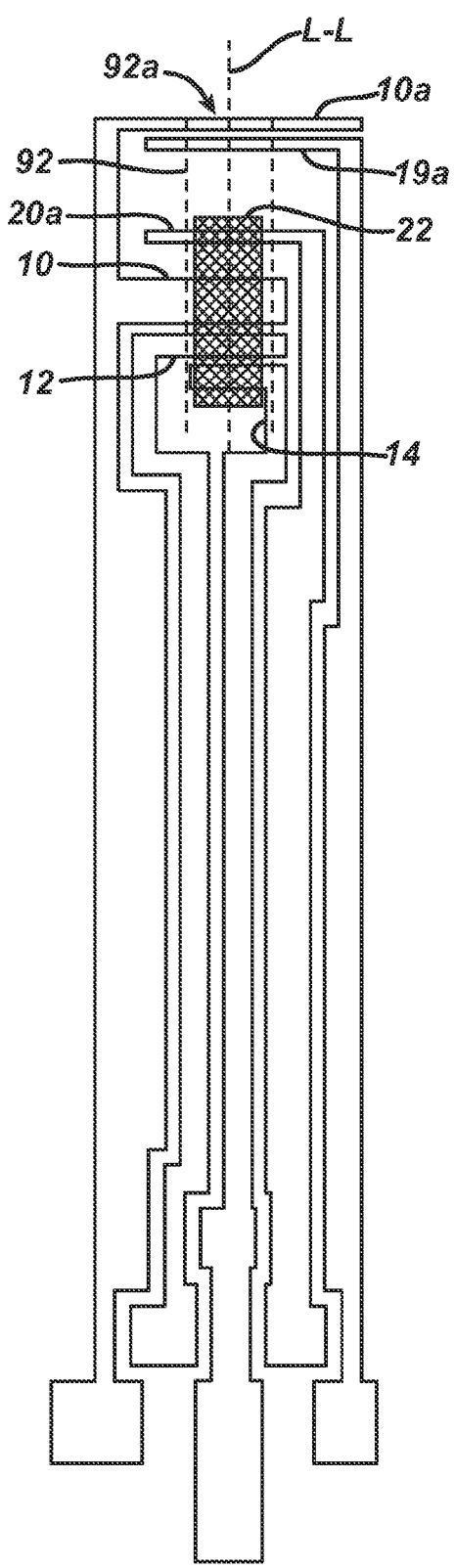
FIG. 3C illustrates a variation of the test strip of FIG. 3B in which a reagent area has been extended upstream to cover at least one of the physical characteristic sensing electrodes.
Figure 3D:
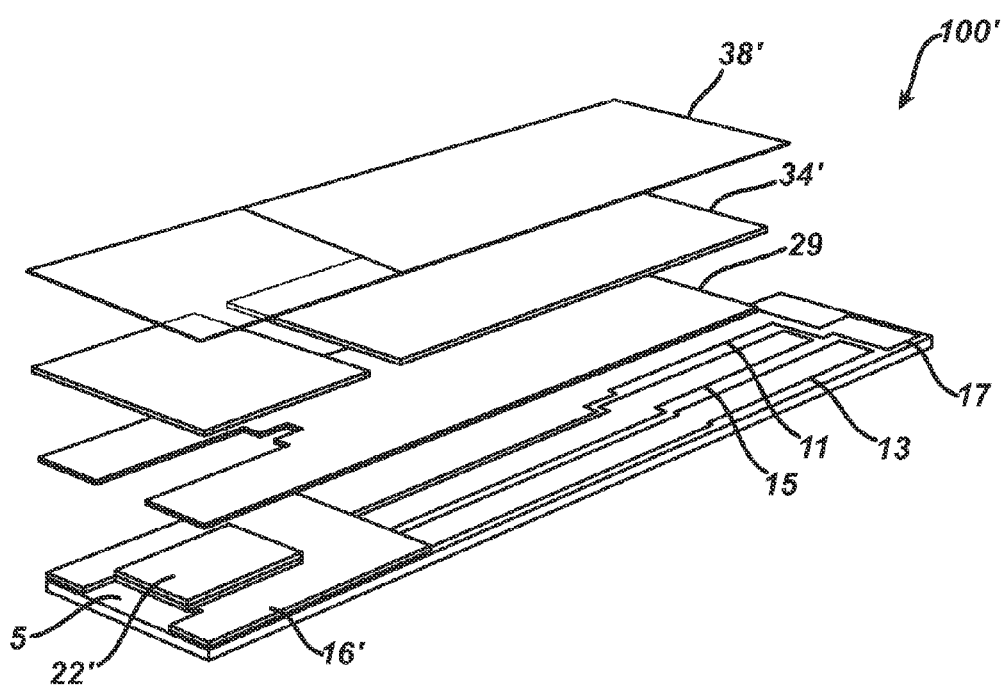
FIG. 3D illustrates a variation of test strip 100 of FIGS. 3A, 3B and 3C in which certain components of the test strip have been integrated together into a single unit.
Figure 3E:
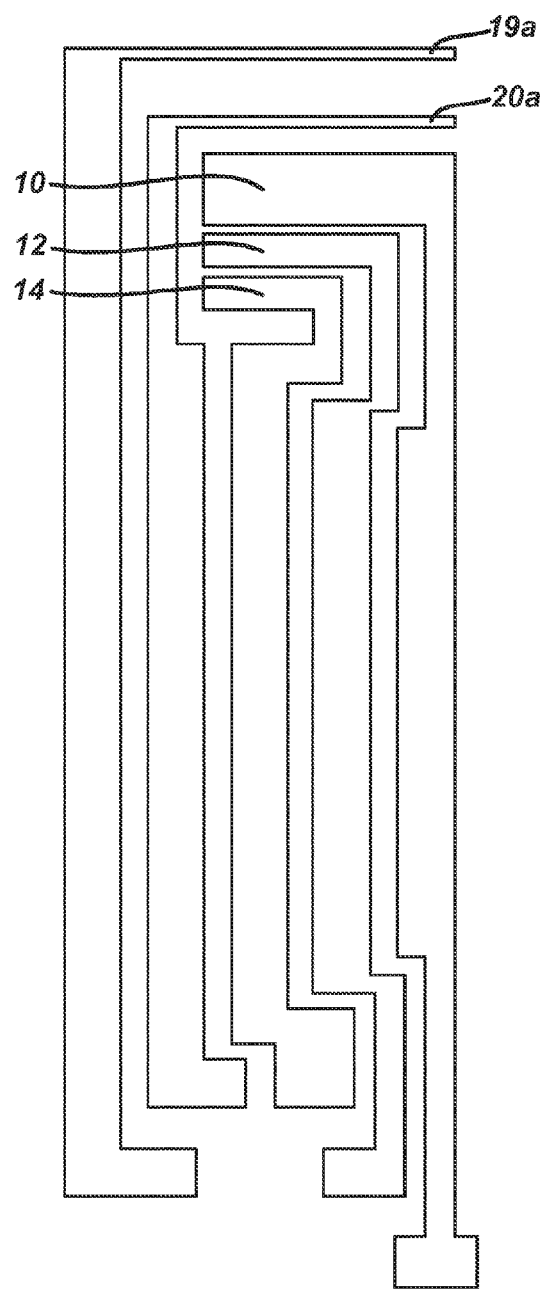
FIGS. 3E and 3F illustrate a physical characteristic sensing electrodes arrangement similar to that of FIG. 3A, 3B, 3C, or 3D, in which the pair of physical characteristic sensing electrodes are proximate the entrance of the test chamber.
Figure 3F:
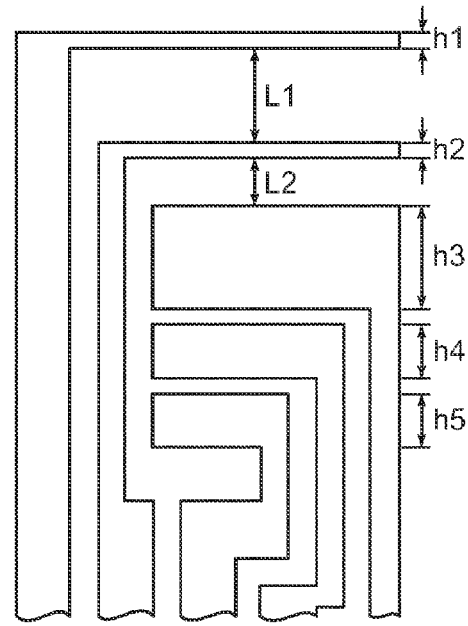

In alternate version of test strip 100, shown here in FIG. 3D, the top layer 38, hydrophilic film layer 34 and spacer 29 have been combined together to form an integrated assembly for mounting to the substrate 5 with reagent layer 22' disposed proximate insulation layer 16'.

In the embodiment of FIG. 3B, the analyte measurement electrodes 10, 12, and 14 are disposed in generally the same configuration as in FIG. 3A, 3C, or 3D. Alternatively, the electrodes to sense physical characteristic (e.g., hematocrit) level, can be disposed in a spaced apart configuration in which one electrode 19a is proximate an entrance 92a to the test chamber 92 and another electrode 20a is at the opposite end of the test chamber 92 (shown in FIG. 3B of the Priority applications) or both sensing electrodes being distal from the entrance 92a (shown in FIGS. 3C and 3D of the Priority applications). At least one of the electrodes on the biosensor is disposed to be in contact with a reagent layer 22.

In FIGS. 3C, 3D, 3E and 3F, the physical characteristic (e.g., hematocrit) sensing electrodes 19a and 20a are disposed adjacent each other and may be placed at the opposite end of the entrance 92a to the test chamber 92 adjacent and downstream of electrode 14 along axis L-L or adjacent the entrance 92a (FIGS. 3A-3E and 3F). In all of these embodiments, the physical characteristic sensing electrodes are spaced apart from the reagent layer 22 so that these physical characteristic sensing electrodes are not impacted by the electrochemical reaction of the reagent in the presence of a fluid sample (e.g., blood or interstitial fluid) containing glucose.

As is known, conventional electrochemical-based analyte test strips employ a working electrode along with an associated counter/reference electrode and enzymatic reagent layer to facilitate an electrochemical reaction with an analyte of interest and, thereby, determine the presence and/or concentration of that analyte. For example, an electrochemical-based analyte test strip for the determination of glucose concentration in a fluid sample can employ an enzymatic reagent that includes the enzyme glucose oxidase and the mediator ferricyanide (which is reduced to the mediator ferrocyanide during the electrochemical reaction). Such conventional analyte test strips and enzymatic reagent layers are described in, for example, U.S. Pat. Nos. 5,708,247; 5,951,836; 6,241,862; and 6,284,125; each of which is hereby incorporated by reference herein to this application. In this regard, the reagent layer employed in various embodiments provided herein can include any suitable sample-soluble enzymatic reagents, with the selection of enzymatic reagents being dependent on the analyte to be determined and the bodily fluid sample. For example, if glucose is to be determined in a fluid sample, enzymatic reagent layer 22 can include glucose oxidase or glucose dehydrogenase along with other components necessary for functional operation.

In general, enzymatic reagent layer 22 includes at least an enzyme and a mediator. Examples of suitable mediators include, for example, ruthenium, Hexaammine Ruthenium (III) Chloride, ferricyanide, ferrocene, ferrocene derivatives, osmium bipyridyl complexes, and quinone derivatives. Examples of suitable enzymes include glucose oxidase, glucose dehydrogenase (GDH) using a pyrroloquinoline quinone (PQQ) co-factor, GDH using a nicotinamide adenine dinucleotide (NAD) co-factor, and GDH using a flavin adenine dinucleotide (FAD) co-factor. Enzymatic reagent layer 22 can be applied during manufacturing using any suitable technique including, for example, screen printing.

Applicants note that enzymatic reagent layer may also contain suitable buffers (such as, for example, Tris HCl, Citraconate, Citrate and Phosphate), hydroxyethylcelulose [HEC], carboxymethylcellulose, ethycellulose and alginate, enzyme stabilizers and other additives as are known in the field.

Further details regarding the use of electrodes and enzymatic reagent layers for the determination of the concentrations of analytes in a bodily fluid sample, albeit in the absence of the phase-shift measurement electrodes, analytical test strips and related methods described herein, are in U.S. Pat. No. 6,733,655, which is hereby fully incorporated by reference herein to this application.

In the various embodiments of the test strip, there are two measurements that are made to a fluid sample deposited on the test strip. One measurement is that of the concentration of the analyte (e.g. glucose) in the fluid sample while the other is that of physical characteristic (e.g., hematocrit) in the same sample. The measurement of the physical characteristic (e.g., hematocrit) is used to modify or correct the glucose measurement so as to remove or reduce the effect of red blood cells on the glucose measurements. Both measurements (glucose and hematocrit) can be performed in sequence, simultaneously or overlapping in duration. For example, the glucose measurement can be performed first then the physical characteristic (e.g., hematocrit); the physical characteristic (e.g., hematocrit) measurement first then the glucose measurement; both measurements at the same time; or a duration of one measurement may overlap a duration of the other measurement. Each measurement is discussed in detail as follow with respect to FIGS. 4A and 4B.

Figure 4A:
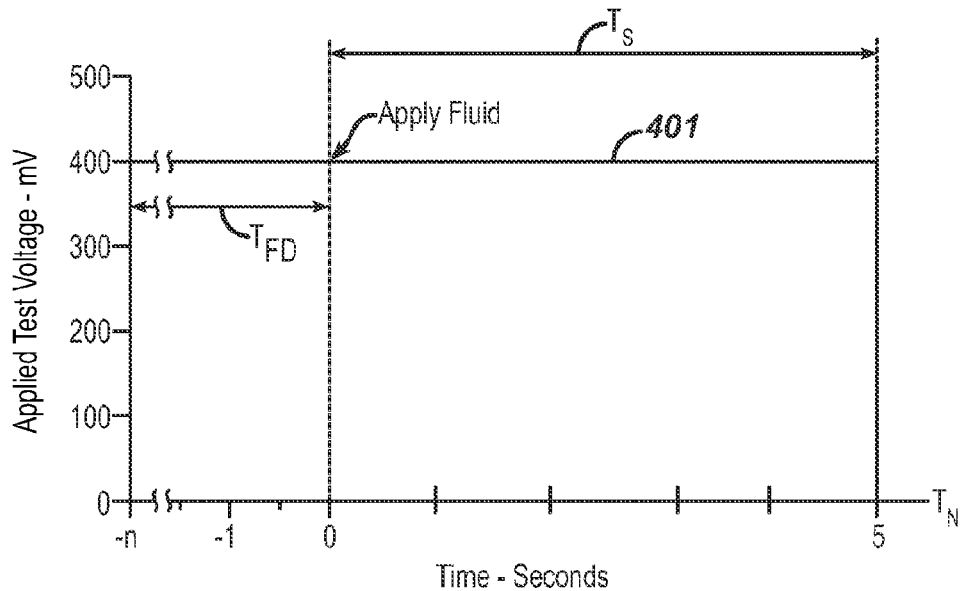
FIG. 4A illustrates a graph of time over applied potential to the test strip of FIG. 1.

FIG. 4A is an exemplary chart of a test signal applied to test strip 100 and its variations shown here in FIGS. 3A-3F. Before a fluid sample is applied to test strip 100 (or its variants in the Priority applications), test meter 200 is in a fluid detection mode in which a first test signal of about 400 millivolts is applied between second working electrode and reference electrode. A second test signal 401 of about 400 millivolts is preferably applied simultaneously between first working electrode (e.g., electrode 12 of strip 100) and reference electrode (e.g., electrode 10 of strip 100). Alternatively, the second test signal may also be applied contemporaneously such that a time interval of the application of the first test signal overlaps with a time interval in the application of the second test voltage. The test meter may be in a fluid detection mode during fluid detection time interval $T_{FD}$ prior to the detection of physiological fluid at starting time at zero. In the fluid detection mode, test meter 200 determines when a fluid is applied to test strip 100 (or its variants in the Priority applications) such that the fluid wets either first working electrode 12 or second working electrode 14 and reference electrode 10. Once test meter 200 recognizes that the physiological fluid has been applied because of, for example, a sufficient increase in the measured test current at either the first working electrode 12 or second working electrode 14 (or both electrodes) with respect to the reference electrode 10, test meter 200 assigns a zero second marker at zero time "0" and starts the test sequence time interval $T_S$. Test meter 200 may sample the current transient output at a suitable sampling rate, such as, for example, every 1 milliseconds to every 100 milliseconds. Upon the completion of the test time interval $T_S$, the test signal is removed. For simplicity, FIG. 4A only shows the first test signal 401 applied to test strip 100 (or its variants in the Priority applications).

Hereafter, a description of how glucose concentration is determined from the known current transients (e.g., the measured electrical current response in nanoamperes as a function of time) that are measured when the test voltages of FIG. 4A are applied to the test strip 100 (or its variants in the Priority applications).

Figure 4B:
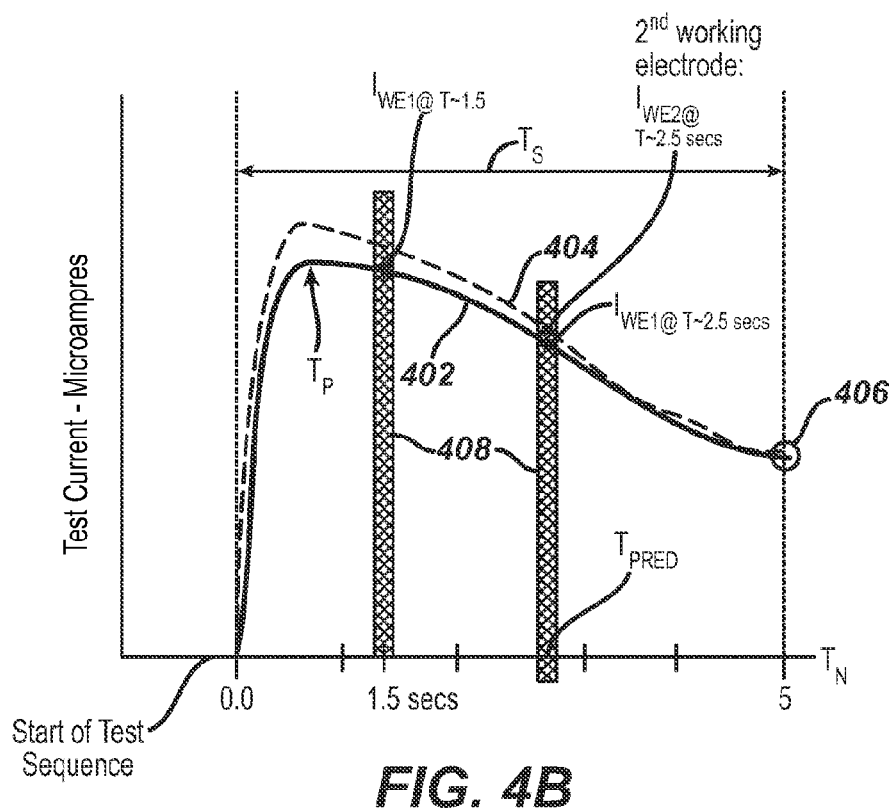
FIG. 4B illustrates a graph of time over output signal from the test strip of FIG. 1.

In FIG. 4A, the first and second test voltages applied to test strip 100 (or its variants in the Priority applications) are generally from about +100 millivolts to about +600 millivolts. In one embodiment in which the electrodes include carbon ink and the mediator includes ferricyanide, the test signal is about +400 millivolts. Other mediator and electrode material combinations will require different test voltages, as is known to those skilled in the art. The duration of the test voltages is generally from about 1 to about 5 seconds after a reaction period and is typically about 3 seconds after a reaction period. Typically, test sequence time $T_S$ is measured relative to time $t_0$. As the voltage 401 is maintained in FIG. 4A for the duration of $T_S$, output signals are generated, shown here in FIG. 4B with the current transient 402 for the first working electrode 12 being generated starting at zero time and likewise the current transient 404 for the second working electrode 14 is also generated with respect to the zero time. It is noted that while the signal transients 402 and 404 have been placed on the same referential zero point for purposes of explaining the process, in physical term, there is a slight time differential between the two signals due to fluid flow in the chamber towards each of the working electrodes 12 and 14 along axis L-L. However, the current transients are sampled and configured in the microcontroller to have the same start time. In FIG. 4B, the current transients build up to a peak proximate peak time $T_p$ at which time, the current slowly drops off until approximately one of 2.5 seconds or 5 seconds after zero time. At the point 406, approximately at 5 seconds, the output signal for each of the working electrodes 12 and 14 may be measured and added together. Alternatively, the signal from only one of the working electrodes 12 and 14 can be doubled. From knowledge of the parameters of the test strip (e.g., batch calibration code offset and batch slope) for the particular test strip 100 and its variations, the analyte (e.g., glucose) concentration can be calculated. Output transient 402 and 404 can be sampled to derive signals $I_E$ (by summation of each of the current $I_{WE1}$ and $I_{WE2}$ or doubling of one of $I_{WE1}$ or $I_{WE2}$) at various time positions during the test sequence.

It is noted that "Intercept" and "Slope" are the parametric values of the biosensor obtained by measuring calibration data from a lot or batch of test strips. Typically around 1500 strips are selected at random from the lot or batch. Physiological fluid (e.g., blood) from donors is spiked to various analyte levels, typically six different glucose concentrations. Typically, blood from 12 different donors is spiked to each of the six levels. Eight strips are given blood from identical donors and levels so that a total of 12×6×8=576 tests are conducted for that lot. These are benchmarked against actual analyte level (e.g., blood glucose concentration) by measuring these using a standard laboratory analyzer such as Yellow Springs Instrument (YSI). A graph of measured glucose concentration is plotted against actual glucose concentration (or measured current versus YSI current) and a formula y=mx+c least squares fitted to the graph to give a value for batch slope m and batch intercept c for the remaining strips from the lot or batch. The applicants have also provided methods and systems in which the batch slope is derived during the determination of an analyte concentration. The "batch slope", or "Slope", may therefore be defined as the measured or derived gradient of the line of best fit for a graph of measured glucose concentration plotted against actual glucose concentration (or measured current versus YSI current). The "batch intercept", or "Intercept", may therefore be defined as the point at which the line of best fit for a graph of measured glucose concentration plotted against actual glucose concentration (or measured current versus YSI current) meets the y axis.

It is worthwhile here to note that the various components, systems and procedures described earlier allow for applicants to provide an analyte measurement system that heretofore was not available in the art. In particular, this system includes a test strip that has a substrate and a plurality of electrodes connected to respective electrode connectors. The system further includes an analyte meter 200 that has a housing, a test strip port connector configured to connect to the respective electrode connectors of the test strip, and a microcontroller 300, shown here in FIG. 2B. The microprocessor 300 is in electrical communication with the test strip port connector 220 to apply electrical signals or sense electrical signals from the plurality of electrodes.

Figure 2B:
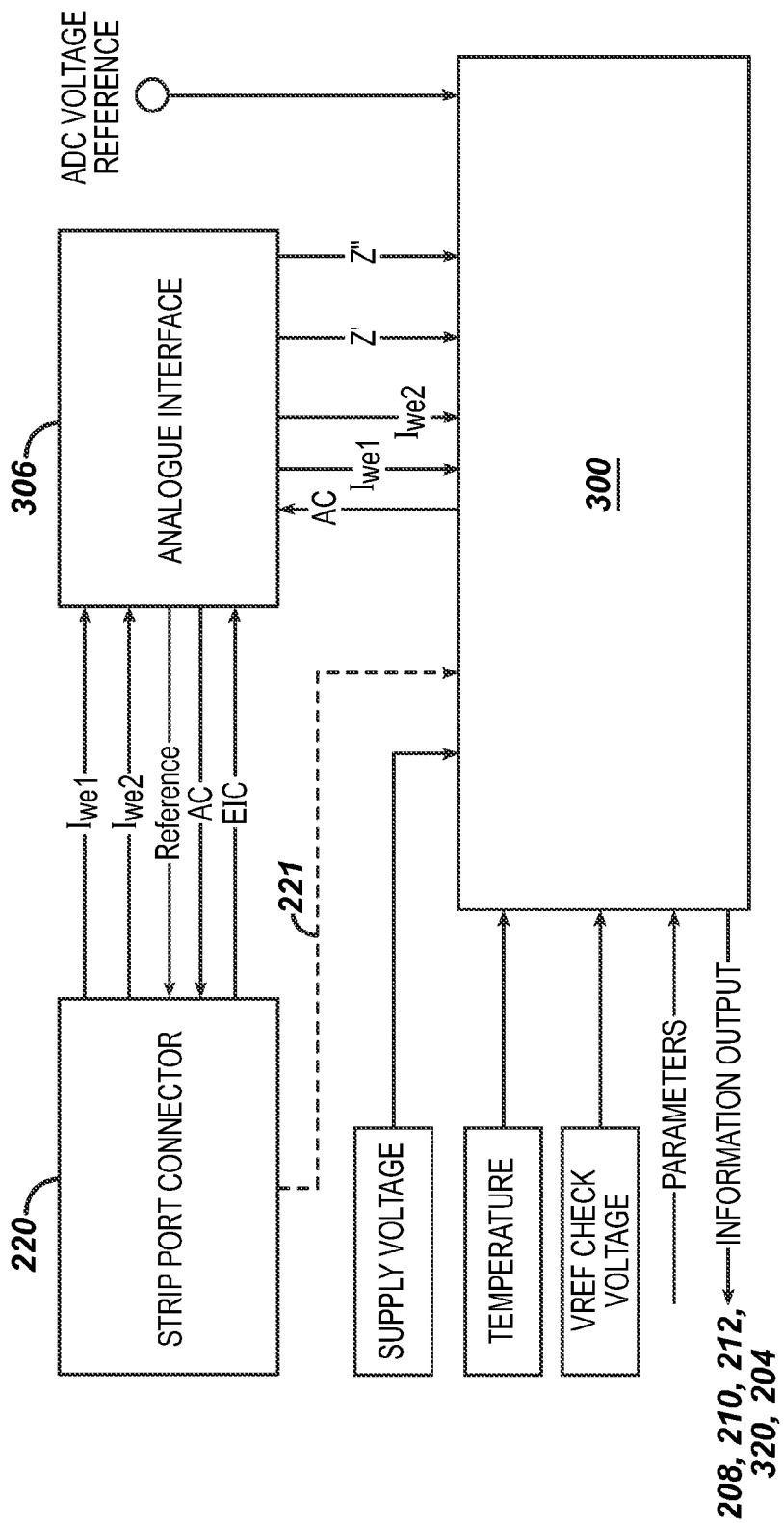
FIG. 2B illustrates in simplified schematic a preferred implementation of a variation of meter 200.

Referring to FIG. 2B, details of a preferred implementation of meter 200 where the same numerals in FIGS. 2A and 2B have a common description. In FIG. 2B, a strip port connector 220 is connected to the analogue interface 306 by five lines including an impedance sensing line EIC to receive signals from physical characteristic sensing electrode(s), alternating signal line AC driving signals to the physical characteristic sensing electrode(s), reference line for a reference electrode, and current sensing lines from respective working electrode 1 and working electrode 2. A strip detection line 221 can also be provided for the connector 220 to indicate insertion of a test strip. The analog interface 306 provides four inputs to the processor 300: (1) real impedance Z'; (2) imaginary impedance Z"; (3) output signal sampled or measured from working electrode 1 of the biosensor or $I_{we1}$; (4) output signal sampled or measured from working electrode 2 of the biosensor or $I_{we1}$. There is one output from the processor 300 to the interface 306 to drive an oscillating signal AC of any value from 25 kHz to about 250 kHz or higher to the physical characteristic sensing electrodes. A phase differential P (in degrees) can be determined from the real impedance Z' and imaginary impedance Z" where:

$$P=\tan^{-1}\{Z''/Z'\} \qquad \text{Eq. 3.1}$$

and magnitude M (in ohms and conventionally written as |Z|) from line Z' and Z" of the interface 306 can be determined where $$M=\sqrt{(Z')^2+(Z'')^2} \qquad \text{Eq. 3.2}$$

In this system, the microprocessor is configured to: (a) apply a first signal to the plurality of electrodes so that a batch slope defined by a physical characteristic of a fluid sample is derived and (b) apply a second signal to the plurality of electrodes so that an analyte concentration is determined based on the derived batch slope. For this system, the plurality of electrodes of the test strip or biosensor includes at least two electrodes to measure the physical characteristic and at least two other electrodes to measure the analyte concentration. For example, the at least two electrodes and the at least two other electrodes are disposed in the same chamber provided on the substrate. Alternatively, the at least two electrodes and the at least two other electrodes are disposed in different chambers provided on the substrate. It is noted that for some embodiments, all of the electrodes are disposed on the same plane defined by the substrate. In particular, in some of the embodiments described herein, a reagent is disposed proximate the at least two other electrodes and no reagent is disposed on the at least two electrodes. One feature of note in this system is the ability to provide for an accurate analyte measurement within about 10 seconds of deposition of a fluid sample (which may be a physiological sample) onto the biosensor as part of the test sequence.

As an example of an analyte calculation (e.g., glucose) for strip 100 (FIG. 3A-3F and its variants in the Priority applications), it is assumed in FIG. 4B that the sampled output signal at 406 for the first working electrode 12 is about 1600 nanoamperes whereas the output signal at 406 for the second working electrode 14 is about 1300 nanoamperes and the calibration code of the test strip indicates that the Intercept is about 500 nanoamperes and the Slope is about 18 nanoamperes/mg/dL. Glucose concentration $G_0$ can be thereafter be determined from Equation 3.3 as follow:

$$G_0=[(I_E)-\text{Intercept}]/\text{Slope} \qquad \text{Eq. 3.3}$$

where $I_E$ is a signal (e.g., current proportional to analyte concentration) which could be the total current from all of the electrodes in the biosensor (e.g., from all five electrodes in sensor 100, both working electrodes 12 and 14 (where $I_E=I_{we1}+I_{we2}$ or $I_E=2*(I_{we1}+I_{we2})/2)$) or alternatively from one of the working electrodes where $I_E=2*I_{we1}$ or $I_E=2*I_{we2}$;

$I_{we1}$ is the signal (e.g., current) measured for the first working electrode at the set sampling time;

$I_{we2}$ is the signal (e.g., current) measured for the second working electrode at the set sampling time;

Slope is the value obtained from calibration testing of a batch of test strips of which this particular strip comes from;

Intercept is the value obtained from calibration testing of a batch of test strips of which this particular strip comes from.

From Eq. 3.3; $G_0=[(1600+1300)-500]/18$ and therefore, $G_0\sim 133$ mg/dL.

It is noted here that the examples have been given in relation to a biosensor 100 which has two working electrodes (12 and 14 in FIGS. 3A-3F and its variants in the Priority applications) such that the measured signals from respective working electrodes have been added together to provide for a total measured current $I_E$, the signal resulting from only one of the two working electrodes can be multiplied by two in a variation of test strip 100 where there is only one working electrode (either electrode 12 or 14). Instead of a total measured signal, an average of the signal from each working electrode can be used as the total measured signal $I_E$ for Equations 3.3, 5, 6, 6.1, 7, and 7.1 described herein, and of course, with appropriate modification to the operational coefficients (as known to those skilled in the art) to account for a lower total measured signal $I_E$ than as compared to an embodiment where the measured signals are added together. Alternatively, the average of the measured signals can be multiplied by two and used as $I_E$ in Equations 3.3, 5, 6, 6.1, 7, and 7.1 without the necessity of deriving the operational coefficients as in the prior example. It is noted that the analyte (e.g., glucose) concentration here is not corrected for any physical characteristic (e.g., hematocrit value) and that certain offsets may be provided to the signal values $I_{we1}$ and $I_{we2}$ to account for errors or delay time in the electrical circuit of the meter 200. Temperature compensation can also be utilized to ensure that the results are calibrated to a referential temperature such as for example room temperature of about 20 degrees Celsius.

Figure 5:
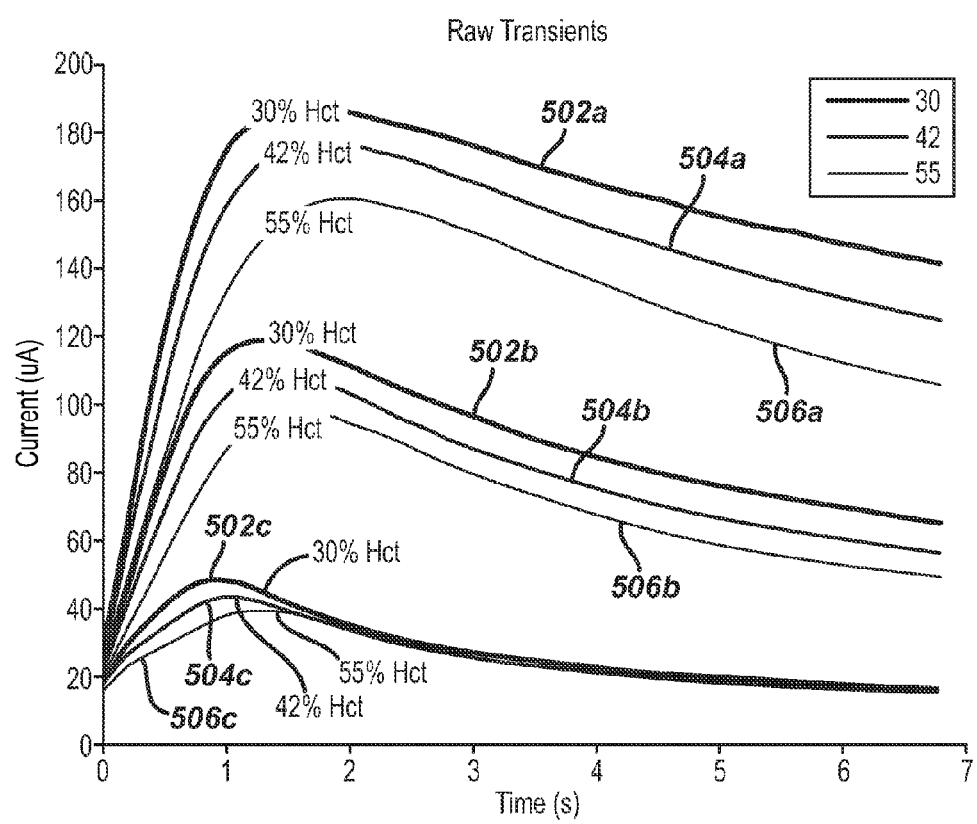
FIG. 5 illustrates the relationship between the parameters of the biosensor and physical characteristic of the fluid sample.

We have found that the existing glucose test strip made by LifeScan (marketed under the Ultra brand) has variations in the current output transients depending on the glucose concentration and hematocrit. These variations can be seen in FIG. 5 in which at high level of glucose (502a, 504a, 506a) or mid-level of glucose (502b, 504b, 506b) the current transient varies distinctly as a function of the physical characteristic (e.g., hematocrit) level and at low glucose level (502c, 504c, 506c) the current transient does not vary as distinctly as in the high glucose or the middle glucose as a function of hematocrit. Specifically, at the high glucose levels, the current transients 502a, 504a, 506a (for 30%, 42% and 55% Hct) maintain a generally consistent separation in current output over time after the peak at about 1.5 seconds after the start of the test sequence. Similarly, at the middle-glucose levels, the current transients 502b, 504b, and 506b (for 30%, 42%, and 55% Hct) maintains a consistent separation in current output over time after the peak at about 1.5 seconds after the start of the test sequence. At the low-glucose levels, the current transients 502c, 504c, and 506c (for 30%, 42%, and 55% Hct) generally converge together after the peak at about 1.5 seconds after the start of the test sequence.

Based on these observations, applicants have found that a relationship exists between the parameters (e.g., batch intercept or batch slope) of these test strips tested at the Lo-G, middle-glucose levels 502b, 504b, 506b, and Hi-G levels with respect to 30%, 42%, and 55% hematocrit levels. In particular, applicants have found that the test strip parameters (e.g., batch intercept or batch slope) are related to hematocrit level from regression analysis. As a consequence, by knowing the physical characteristic of the sample (e.g., hematocrit) and the regression analysis for the biosensor, this relationship can be exploited to allow the strip parameters (e.g., batch intercept or batch slope) to accommodate the different levels of physical characteristic (e.g., hematocrit) so as to achieve much more accurate glucose concentration measurements heretofore unavailable to this type of biosensors.

Now that a glucose concentration ($G_0$) can be determined from the signal $I_E$, a description of applicant's technique to determine the physical characteristic IC (e.g., hematocrit, temperature, viscosity, density and the like) of the fluid sample is provided in relation to FIG. 2B. In FIG. 2B, the system 200 (FIGS. 2A and 2B) applies a first oscillating input signal AC (FIG. 2B) at a first frequency (e.g., of about 25 kilo-Hertz or higher) to at least one of the sensing electrodes. The system is also set up to measure or detect a first oscillating output signal EIC, which in particular involves measuring a first time differential $\Delta t_1$ between the first input and output oscillating signals. At the same time or during overlapping time durations, the system may also apply a second oscillating input signal AC (not shown for brevity) at a second frequency (e.g., about 100 kilo-Hertz to about 1 MegaHertz or higher, and preferably about 250 kilo Hertz) to a pair of electrodes and then measure or detect a second oscillating output signal, which may involve measuring a second time differential $\Delta t_2$ (not shown) between the first input and output oscillating signals. From these signals (AC and EIC), the system estimates a physical characteristic (e.g., hematocrit, viscosity, temperature, density and the like) of the fluid sample based on the first and second time differentials $\Delta t_1$ and $\Delta t_2$. The estimate of the physical characteristic can be attained by applying an equation of the form $$HCT_{EST} = \frac{(C_1 \Delta t_1 - C_2 \Delta t_2 - C_3)}{m_1} \qquad \text{Eq. 4.1}$$

where each of $C_1$, $C_2$, and $C_3$ is an operational constant for the test strip and $m_1$ represent a parameter from regressions data.

Details of this exemplary technique can be found in Provisional U.S. Patent Application Ser. No. 61/530,795 filed on Sep. 2, 2011, entitled, "Hematocrit Corrected Glucose Measurements for Electrochemical Test Strip Using Time Differential of the Signals", which is hereby incorporated by reference.

Another technique to determine physical characteristic (e.g., hematocrit) can be by two independent measurements of physical characteristic (e.g., hematocrit). This can be obtained by determining. (a) the impedance of the fluid sample at a first frequency and (b) the phase angle of the fluid sample at a second frequency substantially higher than the first frequency. In this technique, the fluid sample is modeled as a circuit having unknown reactance and unknown resistance. With this model, an impedance (as signified by notation "|Z|") for measurement (a) can be determined from the applied voltage, the voltage across a known resistor (e.g., the intrinsic strip resistance), and the voltage across the unknown impedance Vz; and similarly, for measurement (b) the phase angle can be measured from a time difference between the input and output signals by those skilled in the art. Details of this technique is shown and described in pending provisional patent application Ser. No. 61/530,808 filed Sep. 2, 2011, which is incorporated by reference. Other suitable techniques for determining the physical characteristic (e.g., hematocrit, viscosity, or density) of the fluid sample can also be utilized such as, for example, U.S. Pat. No. 4,919,770, U.S. Pat. No. 7,972,861, US Patent Application Publication Nos. 2010/0206749, 2009/0223834, or "Electric Cell-Substrate Impedance Sensing (ECIS) as a Noninvasive Means to Monitor the Kinetics of Cell Spreading to Artificial Surfaces" by Joachim Wegener, Charles R. Keese, and Ivar Giaever and published by Experimental Cell Research 259, 158-166 (2000) doi: 10.1006/excr.2000.4919, available online at http://www.idealibrary.com; "Utilization of AC Impedance Measurements for Electrochemical Glucose Sensing Using Glucose Oxidase to Improve Detection Selectivity" by Takuya Kohma, Hidefumi Hasegawa, Daisuke Oyamatsu, and Susumu Kuwabata and published by Bull. Chem. Soc. Jpn. Vol. 80, No. 1, 158-165 (2007), all of these documents are incorporated by reference.

Another technique to determine the physical characteristic can be obtained by knowing the phase difference (e.g., phase angle) and magnitude of the impedance of the sample. In one example, the following relationship is provided for the estimate of the physical characteristic or impedance characteristic of the sample ("IC"):

$$IC = M^2 {}^*y_1 + M^* y_2 + y_3 + P^2 {}^*y_4 + P^* y_5 \qquad \text{Eq. 4.2}$$

where: M represents a magnitude |Z| of a measured impedance in ohms);

P represents a phase difference between the input and output signals (in degrees)

$y_1$ is about −3.2e−08 and ±10%, 5% or 1% of the numerical value provided hereof (and depending on the frequency of the input signal, can be zero);

$y_2$ is about 4.1e−03 and ±10%, 5% or 1% of the numerical value provided hereof (and depending on the frequency of the input signal, can be zero);

$y_3$ is about −2.5e+01 and ±10%, 5% or 1% of the numerical value provided hereof;

$y_4$ is about 1.5e−01 and ±10%, 5% or 1% of the numerical value provided hereof (and depending on the frequency of the input signal, can be zero); and $y_5$ is about 5.0 and ±10%, 5% or 1% of the numerical value provided hereof (and depending on the frequency of the input signal, can be zero).

It is noted here that where the frequency of the input AC signal is high (e.g., greater than 75 kHz) then the parametric terms $y_1$ and $y_2$ relating to the magnitude of impedance M may be ±200% of the exemplary values given herein such that each of the parametric terms may include zero or even a negative value. On the other hand, where the frequency of the AC input signal is low (e.g., less than 75 kHz), the parametric terms $y_4$ and $y_5$ relating to the phase angle P may be ±200% of the exemplary values given herein such that each of the parametric terms may include zero or even a negative value. It is noted here that a magnitude of H or HCT, as used herein, is generally equal to the magnitude of IC. In one exemplary implementation, H or HCT is equal to IC as H or HCT is used herein this application.

In another alternative implementation, Equation 4.3 is provided. Equation 4.3 is the exact derivation of the quadratic relationship, without using phase angles as in Equation 4.2.

$$IC = \frac{-y_2 + \left|\sqrt{y_2^2 - (4y_3(y_1 - M))}\right|}{2y_1} \quad \text{Eq. 4.3}$$

where:
IC is the Impedance Characteristic [%];
M is the magnitude of impedance [Ohm];

$y_1$ is about 1.2292e1 and ±10%, 5% or 1% of the numerical value provided hereof;
$y_2$ is about −4.3431e2 and ±10%, 5% or 1% of the numerical value provided hereof;
$y_3$ is about 3.5260e4 and ±10%, 5% or 1% of the numerical value provided hereof.

By virtue of the various components, systems and insights provided herein, at least four techniques of determining an analyte concentration from a fluid sample (which may be a physiological sample) (and variations of such method) have been achieved by applicants with greater accuracy than heretofore.

Figure 6:
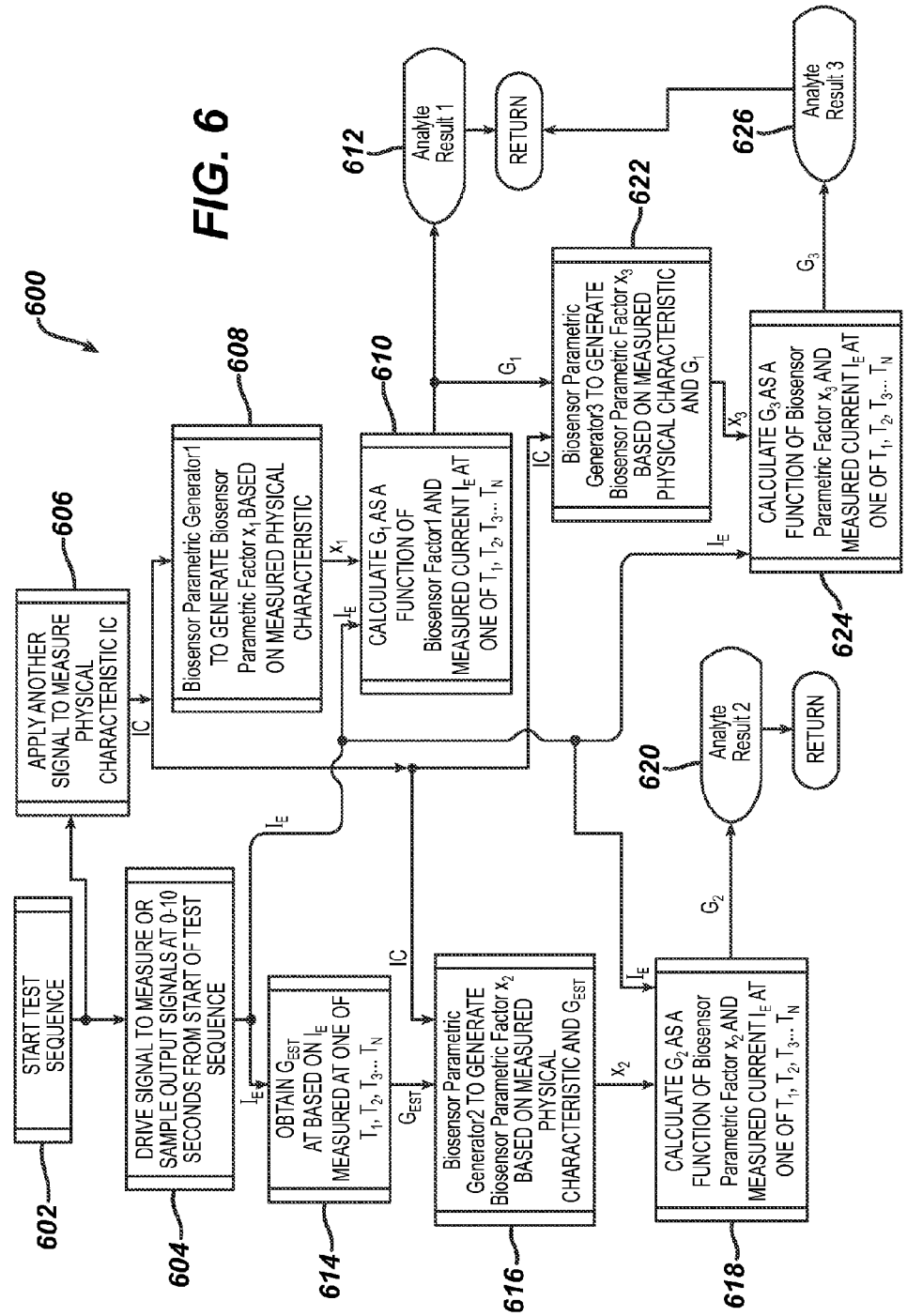
FIG. 6 illustrates an overall system diagram of various modules that embodies at least three techniques for determining analyte concentration.

One of the implementations of the disclosure can be understood with reference to FIG. 6 and in particular the system module 600. In system module 600, it is assumed that a user has deposited a fluid sample at module 602 and sufficient output signal has been detected (FIG. 4B) to initiate the test sequence timer $T_N$. At module 604, the system (FIG. 2B) drives a signal to measure or sample the output signals $I_E$ from at least one the working electrodes (12 and 14) at any one of a plurality of time points or positions $T_1, T_2, T_3, \ldots T_N$. As can be seen in FIG. 4B, the time positions can be any time point or interval in the test sequence $T_S$. For example, the time position at which the output signal is measured can be a single time position $T_{1.5}$ at 1.5 seconds or an interval 408 (e.g., interval~10 milliseconds or more depending on the sampling rate of the system) overlapping the time position $T_{2.8}$ proximate 2.8 seconds.

Returning to FIG. 6, at the same time, after or even before the driving of the signal in module 604, the system may also apply another signal to measure the physical characteristic IC of the sample in module 606. The signal IC is provided to a Biosensor Parametric Generator 608 which could be a look-up table or a matrix configured to provide a new parameter of the biosensor ($x_1$), which may be a new batch slope or a batch intercept for the biosensor 100. The output of the generator 608 is provided to a calculation module 610, along with output signal $I_E$ measured at one of the plurality of predetermined time positions. The calculation module 610 is configured to provide a first analyte concentration for annunciator 612 to inform the user of the first analyte result.

For the generator module 608, the system may utilize the following exemplary Table 1. In Table 1, the impedance characteristic of the sample, which in this case is designated as estimated percent hematocrit is correlated to a new biosensor parametric factor $x_1$ (relating to batch slope) based on historical regression analysis of batches of the biosensor.

TABLE 1A

| | IC~estimated hematocrits | | | | | | | | | | | | |
|---|---|---|---|---|---|---|---|---|---|---|---|---|---|
| | 24% | 27 | 30 | 33 | 36 | 39 | 42 | 45 | 48 | 51 | 54 | 57 | 60% |
| P-Factor $x_1$ | 0.92 | 0.91 | 0.89 | 0.88 | 0.87 | 0.86 | 0.85 | 0.83 | 0.82 | 0.82 | 0.8 | 0.78 | 0.77 |

Once the alternative version of IC in Equation 4.3 is used, there is no need to use IC as expressed in % in the Table 1A. That is, one may substitute IC for magnitude of impedance |Z| expressed in Ohm. This removes the calculation of IC in the system or meter (which saves code space and calculation time, therefore enables lower cost meters to cope better with the task at hand). In this case, Table 1A can be modified into Table 1B:

TABLE 1B

| | Physical Characteristic~Impedance Magnitude or |Z| in Ohms | | | | | | | | | | | | |
|---|---|---|---|---|---|---|---|---|---|---|---|---|---|
| | 31900 | 32500 | 33300 | 34300 | 35600 | 37000 | 38700 | 40600 | 42700 | 45100 | 47700 | 50400 | 53500 |
| P-Factor $x_1$ | 0.92 | 0.91 | 0.89 | 0.88 | 0.87 | 0.86 | 0.85 | 0.83 | 0.82 | 0.82 | 0.8 | 0.78 | 0.77 |

The calculation module 610, on the other hand, is configured to use Equation 5 of the form:

$$G_1 = \left[\frac{I_E - P1}{P2 * x_1}\right] \quad \text{Equation (5)}$$

where $G_1$ represents a first analyte concentration;
$I_E$ represents a total output signal (e.g., current) from at least one electrode measured at one of the plurality of predetermined time positions $T_1, T_2, T_3, \ldots T_N$~test sequence interval (where $T_1$~1.0 sec., $T_2$~1.01 sec., $T_3$~1.02 secs);
P1 represents an intercept parameter of the biosensor;
P2 represents a slope parameter of the biosensor; and
$x_1$ represents a first biosensor parametric factor based on the physical characteristic of the sample (in either Table 1A or 1B).

In Equation 5, for the particular embodiments described herein, P1 is about 475 nanoamps and P2 is about 9.5 nanoamps/(mg/dL).

It is believed that while the results provided by modules 606, 608 and 610 are more accurate than the existing technique, improvements in accuracy can still be obtained. Specifically, the inventors have provided a second alternative technique, shown here in FIG. 6 as modules 602, 604, 606, 614, 616 and 618. As modules 604 and 606 were described earlier as providing for the output signal IE and the physical characteristic signal IC, these modules need not be mentioned in the second technique.

In module 614, the system obtains an estimated analyte concentration ($G_{EST}$) based on the measured output signal at one of a predetermined time positions (e.g., at 2.5 seconds). The estimated analyte concentration ($G_{EST}$) is used along with the physical characteristic signal IC for module 616 to generate a second biosensor parametric factor $x_2$. The parametric factor $x_2$ is based on both the physical characteristic IC and the estimated analyte $G_{EST}$ to arrive at a multiplication factor of the existing biosensor parameter(s) (e.g., the parameter being slope or intercept) in Equation 3.3.

Biosensor parametric factor $x_2$ is determined by historical regression analysis of the biosensors described herein. As such, a curve fitting equation, a matrix or a look-up table can be utilized for module 616 to generate the needed biosensor parametric factor $x_2$. For ease of computation, a look-up table is utilized to reduce the computational load on the processor 300. An exemplary look-up table is shown here in Table 2:

TABLE 2A

Biosensor Parametric Factor $x_2$ based on Physical Characteristic and $G_{est}$

| | | \multicolumn{13}{c}{IC~Estimated Haematocrit [%]} |
|---|---|---|---|---|---|---|---|---|---|---|---|---|---|---|
| | | 24 | 27 | 30 | 33 | 36 | 39 | 42 | 45 | 48 | 51 | 54 | 57 | 60 |
| Glucose | 25 | 0.73 | 0.73 | 0.73 | 0.73 | 0.73 | 0.73 | 0.73 | 0.73 | 0.73 | 0.73 | 0.73 | 0.73 | 0.73 |
| Estimate | 50 | 0.97 | 0.96 | 0.95 | 0.93 | 0.92 | 0.90 | 0.89 | 0.87 | 0.85 | 0.83 | 0.82 | 0.80 | 0.78 |
| ($G_{EST}$) | 75 | 1.09 | 1.07 | 1.05 | 1.03 | 1.01 | 0.99 | 0.96 | 0.93 | 0.91 | 0.88 | 0.85 | 0.82 | 0.78 |
| [mg/dl] | 100 | 1.13 | 1.11 | 1.09 | 1.07 | 1.04 | 1.02 | 0.99 | 0.96 | 0.93 | 0.89 | 0.86 | 0.82 | 0.78 |
| | 125 | 1.15 | 1.13 | 1.11 | 1.09 | 1.06 | 1.03 | 1.00 | 0.97 | 0.93 | 0.90 | 0.86 | 0.82 | 0.78 |
| | 150 | 1.17 | 1.15 | 1.12 | 1.10 | 1.07 | 1.04 | 1.01 | 0.97 | 0.94 | 0.90 | 0.86 | 0.82 | 0.78 |
| | 175 | 1.17 | 1.15 | 1.13 | 1.10 | 1.07 | 1.04 | 1.01 | 0.98 | 0.94 | 0.91 | 0.87 | 0.82 | 0.78 |
| | 200 | 1.18 | 1.16 | 1.13 | 1.11 | 1.08 | 1.05 | 1.02 | 0.98 | 0.94 | 0.91 | 0.87 | 0.82 | 0.78 |
| | 225 | 1.18 | 1.16 | 1.14 | 1.11 | 1.08 | 1.05 | 1.02 | 0.98 | 0.95 | 0.91 | 0.87 | 0.82 | 0.78 |
| | 250 | 1.19 | 1.16 | 1.14 | 1.11 | 1.08 | 1.05 | 1.02 | 0.98 | 0.95 | 0.91 | 0.87 | 0.82 | 0.78 |
| | 275 | 1.19 | 1.17 | 1.14 | 1.11 | 1.08 | 1.05 | 1.02 | 0.98 | 0.95 | 0.91 | 0.87 | 0.82 | 0.78 |
| | 300 | 1.19 | 1.17 | 1.14 | 1.11 | 1.09 | 1.05 | 1.02 | 0.99 | 0.95 | 0.91 | 0.87 | 0.82 | 0.78 |
| | 325 | 1.19 | 1.17 | 1.14 | 1.12 | 1.09 | 1.05 | 1.02 | 0.99 | 0.95 | 0.91 | 0.87 | 0.82 | 0.78 |
| | 350 | 1.19 | 1.17 | 1.14 | 1.12 | 1.09 | 1.06 | 1.02 | 0.99 | 0.95 | 0.91 | 0.87 | 0.82 | 0.78 |
| | 375 | 1.19 | 1.17 | 1.14 | 1.12 | 1.09 | 1.06 | 1.02 | 0.99 | 0.95 | 0.91 | 0.87 | 0.82 | 0.78 |
| | 400 | 1.19 | 1.17 | 1.15 | 1.12 | 1.09 | 1.06 | 1.02 | 0.99 | 0.95 | 0.91 | 0.87 | 0.82 | 0.78 |
| | 425 | 1.19 | 1.17 | 1.15 | 1.12 | 1.09 | 1.06 | 1.02 | 0.99 | 0.95 | 0.91 | 0.87 | 0.82 | 0.78 |
| | 450 | 1.19 | 1.17 | 1.15 | 1.12 | 1.09 | 1.06 | 1.02 | 0.99 | 0.95 | 0.91 | 0.87 | 0.82 | 0.78 |
| | 475 | 1.20 | 1.17 | 1.15 | 1.12 | 1.09 | 1.06 | 1.02 | 0.99 | 0.95 | 0.91 | 0.87 | 0.82 | 0.78 |
| | 500 | 1.20 | 1.17 | 1.15 | 1.12 | 1.09 | 1.06 | 1.02 | 0.99 | 0.95 | 0.91 | 0.87 | 0.82 | 0.78 |
| | 525 | 1.20 | 1.17 | 1.15 | 1.12 | 1.09 | 1.06 | 1.02 | 0.99 | 0.95 | 0.91 | 0.87 | 0.82 | 0.78 |
| | 550 | 1.20 | 1.17 | 1.15 | 1.12 | 1.09 | 1.06 | 1.02 | 0.99 | 0.95 | 0.91 | 0.87 | 0.82 | 0.78 |
| | 575 | 1.20 | 1.17 | 1.15 | 1.12 | 1.09 | 1.06 | 1.02 | 0.99 | 0.95 | 0.91 | 0.87 | 0.82 | 0.78 |
| | 600 | 1.20 | 1.17 | 1.15 | 1.12 | 1.09 | 1.06 | 1.02 | 0.99 | 0.95 | 0.91 | 0.87 | 0.82 | 0.78 |

Similar to the case of Table 1A, if the alternative version of IC in Equation 4.3 is used, there is no need to use IC as expressed in % in the Table 2A. That is, one may substitute IC for magnitude of impedance |Z| expressed in Ohm. This removes the calculation of IC in the system or meter (which saves code space and calculation time, therefore enables lower cost meters to cope better with the task at hand). In this case, Table 2A can be modified into Table 2B:

TABLE 2B

Biosensor Parametric Factor $x_2$ based on Physical Characteristic and $G_{est}$

| | | \multicolumn{13}{c}{Physical Characteristic~Impedance Magnitude or |Z| in Ohms} |
|---|---|---|---|---|---|---|---|---|---|---|---|---|---|---|
| | | 31900 | 32500 | 33300 | 34300 | 35600 | 37000 | 38700 | 40600 | 42700 | 45100 | 47700 | 50400 | 53500 |
| Glucose | 25 | 0.73 | 0.73 | 0.73 | 0.73 | 0.73 | 0.73 | 0.73 | 0.73 | 0.73 | 0.73 | 0.73 | 0.73 | 0.73 |
| Estimate | 50 | 0.97 | 0.96 | 0.95 | 0.93 | 0.92 | 0.90 | 0.89 | 0.87 | 0.85 | 0.83 | 0.82 | 0.80 | 0.78 |
| ($G_{EST}$) | 75 | 1.09 | 1.07 | 1.05 | 1.03 | 1.01 | 0.99 | 0.96 | 0.93 | 0.91 | 0.88 | 0.85 | 0.82 | 0.78 |
| [mg/dl] | 100 | 1.13 | 1.11 | 1.09 | 1.07 | 1.04 | 1.02 | 0.99 | 0.96 | 0.93 | 0.89 | 0.86 | 0.82 | 0.78 |
| | 125 | 1.15 | 1.13 | 1.11 | 1.09 | 1.06 | 1.03 | 1.00 | 0.97 | 0.93 | 0.90 | 0.86 | 0.82 | 0.78 |
| | 150 | 1.17 | 1.15 | 1.12 | 1.10 | 1.07 | 1.04 | 1.01 | 0.97 | 0.94 | 0.90 | 0.86 | 0.82 | 0.78 |
| | 175 | 1.17 | 1.15 | 1.13 | 1.10 | 1.07 | 1.04 | 1.01 | 0.98 | 0.94 | 0.91 | 0.87 | 0.82 | 0.78 |
| | 200 | 1.18 | 1.16 | 1.13 | 1.11 | 1.08 | 1.05 | 1.02 | 0.98 | 0.94 | 0.91 | 0.87 | 0.82 | 0.78 |
| | 225 | 1.18 | 1.16 | 1.14 | 1.11 | 1.08 | 1.05 | 1.02 | 0.98 | 0.95 | 0.91 | 0.87 | 0.82 | 0.78 |
| | 250 | 1.19 | 1.16 | 1.14 | 1.11 | 1.08 | 1.05 | 1.02 | 0.98 | 0.95 | 0.91 | 0.87 | 0.82 | 0.78 |
| | 275 | 1.19 | 1.17 | 1.14 | 1.11 | 1.08 | 1.05 | 1.02 | 0.98 | 0.95 | 0.91 | 0.87 | 0.82 | 0.78 |
| | 300 | 1.19 | 1.17 | 1.14 | 1.11 | 1.09 | 1.05 | 1.02 | 0.99 | 0.95 | 0.91 | 0.87 | 0.82 | 0.78 |

TABLE 2B-continued

Biosensor Parametric Factor $x_2$ based on Physical Characteristic and $G_{est}$

| | Physical Characteristic~Impedance Magnitude or $\|Z\|$ in Ohms | | | | | | | | | | | | |
|---|---|---|---|---|---|---|---|---|---|---|---|---|---|
| | 31900 | 32500 | 33300 | 34300 | 35600 | 37000 | 38700 | 40600 | 42700 | 45100 | 47700 | 50400 | 53500 |
| 325 | 1.19 | 1.17 | 1.14 | 1.12 | 1.09 | 1.05 | 1.02 | 0.99 | 0.95 | 0.91 | 0.87 | 0.82 | 0.78 |
| 350 | 1.19 | 1.17 | 1.14 | 1.12 | 1.09 | 1.06 | 1.02 | 0.99 | 0.95 | 0.91 | 0.87 | 0.82 | 0.78 |
| 375 | 1.19 | 1.17 | 1.14 | 1.12 | 1.09 | 1.06 | 1.02 | 0.99 | 0.95 | 0.91 | 0.87 | 0.82 | 0.78 |
| 400 | 1.19 | 1.17 | 1.15 | 1.12 | 1.09 | 1.06 | 1.02 | 0.99 | 0.95 | 0.91 | 0.87 | 0.82 | 0.78 |
| 425 | 1.19 | 1.17 | 1.15 | 1.12 | 1.09 | 1.06 | 1.02 | 0.99 | 0.95 | 0.91 | 0.87 | 0.82 | 0.78 |
| 450 | 1.19 | 1.17 | 1.15 | 1.12 | 1.09 | 1.06 | 1.02 | 0.99 | 0.95 | 0.91 | 0.87 | 0.82 | 0.78 |
| 475 | 1.20 | 1.17 | 1.15 | 1.12 | 1.09 | 1.06 | 1.02 | 0.99 | 0.95 | 0.91 | 0.87 | 0.82 | 0.78 |
| 500 | 1.20 | 1.17 | 1.15 | 1.12 | 1.09 | 1.06 | 1.02 | 0.99 | 0.95 | 0.91 | 0.87 | 0.82 | 0.78 |
| 525 | 1.20 | 1.17 | 1.15 | 1.12 | 1.09 | 1.06 | 1.02 | 0.99 | 0.95 | 0.91 | 0.87 | 0.82 | 0.78 |
| 550 | 1.20 | 1.17 | 1.15 | 1.12 | 1.09 | 1.06 | 1.02 | 0.99 | 0.95 | 0.91 | 0.87 | 0.82 | 0.78 |
| 575 | 1.20 | 1.17 | 1.15 | 1.12 | 1.09 | 1.06 | 1.02 | 0.99 | 0.95 | 0.91 | 0.87 | 0.82 | 0.78 |
| 600 | 1.20 | 1.17 | 1.15 | 1.12 | 1.09 | 1.06 | 1.02 | 0.99 | 0.95 | 0.91 | 0.87 | 0.82 | 0.78 |

As is well-known to those skilled in the art, where the glucose estimate does not match up to the table, an interpolation can be utilized between the data provided in all of the tables described herein.

Referring back to FIG. 6, module 618 utilizes both the parametric factor $x_2$ (in either Table 2A or 2B) and the measured or sampled output signal $I_E$ to calculate a second analyte concentration $G_2$. The module 618 is configured to use Equation 6 of the form:

$$G_2 = \left[\frac{I_E - P1}{P2 * x_2}\right] \quad \text{Equation (6)}$$

where $G_1$ represents a first analyte concentration;

$I_E$ represents a total output signal (e.g., current) from at least one electrode measured at one of the plurality of predetermined time positions $T_1, T_2, T_3, \ldots T_N$~test sequence interval (where $T_1$~1.0 sec., $T_2$~1.01 sec., $T_3$~1.02 secs);

P1 represents an intercept parameter of the biosensor;

P2 represents a slope parameter of the biosensor, in which P2 is about 9.5 nanoamps/(mg/dL); and $x_2$ represents a second biosensor parametric factor based on the physical characteristic of the sample and the estimated analyte concentration $G_{EST}$ where:

$$G_{EST} = \left[\frac{I_E - P1}{P2}\right] \quad \text{Equation (6.1)}$$

$I_E$ represents a total output signal (e.g., current) from the biosensor measured at one or another of the plurality of predetermined time positions $T_1, T_2, T_3, \ldots T_N$~test sequence interval (where $T_1$~1.0 sec., $T_2$~1.01 sec., $T_3$~1.02 secs);

P1 represents an intercept parameter of the biosensor and

P2 represents a slope parameter of the biosensor.

In the particular embodiments of the strips described herein and the Priority applications, the time position for both Equations 6 and 6.1 is about 5 seconds from the start of the test sequence, where P1 is about 475 nanoamps and P2 is about 9.5 nanoamps/(mg/dL).

Once the module 618 has obtained the second analyte concentration G2, the annunciator module 620 can provide the result to the user.

In a third alternative, shown here in relation to modules 602, 604, 606, 608, 610, 622, 624, and 626, it is believed that this third technique could yield greater improvements as compared to the first and second techniques.

As modules 602, 604, 606, 608, and 610 have been described earlier, these modules need not be mentioned in the third technique. With reference to FIG. 6, module 622 is configured to receive both the first analyte concentration result G1 from module 610 and the physical characteristic from module 606 so that a third parametric factor x3 can be generated. As in module 616, a look-up table, such as, for example, Table 3 can be utilized, however, the inventors do not intend to be limited to a look-up table described herein. In Table 3A, the system can obtain the required factor by correlating the physical characteristic to the analyte concentration $G_1$. For example, where the first analyte concentration is 225 mg/dL and the estimated hematocrit is about 57%, the parametric factor $x_3$ is determined to be 0.82 from Table 3A.

TABLE 3A

Biosensor Parametric Factor $x_3$ based on Physical Characteristic IC and $G_1$

| | | IC~Estimated Haematocrit [%] | | | | | | | | | | | | |
|---|---|---|---|---|---|---|---|---|---|---|---|---|---|---|
| | | 24 | 27 | 30 | 33 | 36 | 39 | 42 | 45 | 48 | 51 | 54 | 57 | 60 |
| $G_1$ [mg/dL] | 25 | 0.73 | 0.73 | 0.73 | 0.73 | 0.73 | 0.73 | 0.73 | 0.73 | 0.73 | 0.73 | 0.73 | 0.73 | 0.73 |
| | 50 | 0.97 | 0.96 | 0.95 | 0.93 | 0.92 | 0.90 | 0.89 | 0.87 | 0.85 | 0.83 | 0.82 | 0.80 | 0.78 |
| | 75 | 1.09 | 1.07 | 1.05 | 1.03 | 1.01 | 0.99 | 0.96 | 0.93 | 0.91 | 0.88 | 0.85 | 0.82 | 0.78 |
| | 100 | 1.13 | 1.11 | 1.09 | 1.07 | 1.04 | 1.02 | 0.99 | 0.96 | 0.93 | 0.89 | 0.86 | 0.82 | 0.78 |
| | 125 | 1.15 | 1.13 | 1.11 | 1.09 | 1.06 | 1.03 | 1.00 | 0.97 | 0.93 | 0.90 | 0.86 | 0.82 | 0.78 |
| | 150 | 1.17 | 1.15 | 1.12 | 1.10 | 1.07 | 1.04 | 1.01 | 0.97 | 0.94 | 0.90 | 0.86 | 0.82 | 0.78 |

TABLE 3A-continued

Biosensor Parametric Factor $x_3$ based on Physical Characteristic IC and $G_1$

IC~Estimated Haematocrit [%]

| | 24 | 27 | 30 | 33 | 36 | 39 | 42 | 45 | 48 | 51 | 54 | 57 | 60 |
|---|---|---|---|---|---|---|---|---|---|---|---|---|---|
| 175 | 1.17 | 1.15 | 1.13 | 1.10 | 1.07 | 1.04 | 1.01 | 0.98 | 0.94 | 0.91 | 0.87 | 0.82 | 0.78 |
| 200 | 1.18 | 1.16 | 1.13 | 1.11 | 1.08 | 1.05 | 1.02 | 0.98 | 0.94 | 0.91 | 0.87 | 0.82 | 0.78 |
| 225 | 1.18 | 1.16 | 1.14 | 1.11 | 1.08 | 1.05 | 1.02 | 0.98 | 0.95 | 0.91 | 0.87 | 0.82 | 0.78 |
| 250 | 1.19 | 1.16 | 1.14 | 1.11 | 1.08 | 1.05 | 1.02 | 0.98 | 0.95 | 0.91 | 0.87 | 0.82 | 0.78 |
| 275 | 1.19 | 1.17 | 1.14 | 1.11 | 1.08 | 1.05 | 1.02 | 0.98 | 0.95 | 0.91 | 0.87 | 0.82 | 0.78 |
| 300 | 1.19 | 1.17 | 1.14 | 1.11 | 1.09 | 1.05 | 1.02 | 0.99 | 0.95 | 0.91 | 0.87 | 0.82 | 0.78 |
| 325 | 1.19 | 1.17 | 1.14 | 1.12 | 1.09 | 1.05 | 1.02 | 0.99 | 0.95 | 0.91 | 0.87 | 0.82 | 0.78 |
| 350 | 1.19 | 1.17 | 1.14 | 1.12 | 1.09 | 1.06 | 1.02 | 0.99 | 0.95 | 0.91 | 0.87 | 0.82 | 0.78 |
| 375 | 1.19 | 1.17 | 1.14 | 1.12 | 1.09 | 1.06 | 1.02 | 0.99 | 0.95 | 0.91 | 0.87 | 0.82 | 0.78 |
| 400 | 1.19 | 1.17 | 1.15 | 1.12 | 1.09 | 1.06 | 1.02 | 0.99 | 0.95 | 0.91 | 0.87 | 0.82 | 0.78 |
| 425 | 1.19 | 1.17 | 1.15 | 1.12 | 1.09 | 1.06 | 1.02 | 0.99 | 0.95 | 0.91 | 0.87 | 0.82 | 0.78 |
| 450 | 1.19 | 1.17 | 1.15 | 1.12 | 1.09 | 1.06 | 1.02 | 0.99 | 0.95 | 0.91 | 0.87 | 0.82 | 0.78 |
| 475 | 1.20 | 1.17 | 1.15 | 1.12 | 1.09 | 1.06 | 1.02 | 0.99 | 0.95 | 0.91 | 0.87 | 0.82 | 0.78 |
| 500 | 1.20 | 1.17 | 1.15 | 1.12 | 1.09 | 1.06 | 1.02 | 0.99 | 0.95 | 0.91 | 0.87 | 0.82 | 0.78 |
| 525 | 1.20 | 1.17 | 1.15 | 1.12 | 1.09 | 1.06 | 1.02 | 0.99 | 0.95 | 0.91 | 0.87 | 0.82 | 0.78 |
| 550 | 1.20 | 1.17 | 1.15 | 1.12 | 1.09 | 1.06 | 1.02 | 0.99 | 0.95 | 0.91 | 0.87 | 0.82 | 0.78 |
| 575 | 1.20 | 1.17 | 1.15 | 1.12 | 1.09 | 1.06 | 1.02 | 0.99 | 0.95 | 0.91 | 0.87 | 0.82 | 0.78 |
| 600 | 1.20 | 1.17 | 1.15 | 1.12 | 1.09 | 1.06 | 1.02 | 0.99 | 0.95 | 0.91 | 0.87 | 0.82 | 0.78 |

Similar to the case of Table 2A, if the alternative version of IC in Equation 4.3 is used, there is no need to use IC as expressed in % in the Table 3A. That is, one may substitute IC for magnitude of impedance |Z| expressed in Ohm. This removes the calculation of IC in the system or meter (which saves code space and calculation time, therefore enables lower cost meters to cope better with the task at hand). In this case, Table 3A can be modified into Table 3B:

TABLE 3B

Biosensor Parametric Factor $x_3$ based on Physical Characteristic and $G_1$

Physical Characteristic~Impedance Magnitude or |Z| in Ohms

| | | 31900 | 32500 | 33300 | 34300 | 35600 | 37000 | 38700 | 40600 | 42700 | 45100 | 47700 | 50400 | 53500 |
|---|---|---|---|---|---|---|---|---|---|---|---|---|---|---|
| $G_1$ | 25 | 0.73 | 0.73 | 0.73 | 0.73 | 0.73 | 0.73 | 0.73 | 0.73 | 0.73 | 0.73 | 0.73 | 0.73 | 0.73 |
| [mg/dL] | 50 | 0.97 | 0.96 | 0.95 | 0.93 | 0.92 | 0.90 | 0.89 | 0.87 | 0.85 | 0.83 | 0.82 | 0.80 | 0.78 |
| | 75 | 1.09 | 1.07 | 1.05 | 1.03 | 1.01 | 0.99 | 0.96 | 0.93 | 0.91 | 0.88 | 0.85 | 0.82 | 0.78 |
| | 100 | 1.13 | 1.11 | 1.09 | 1.07 | 1.04 | 1.02 | 0.99 | 0.96 | 0.93 | 0.89 | 0.86 | 0.82 | 0.78 |
| | 125 | 1.15 | 1.13 | 1.11 | 1.09 | 1.06 | 1.03 | 1.00 | 0.97 | 0.93 | 0.90 | 0.86 | 0.82 | 0.78 |
| | 150 | 1.17 | 1.15 | 1.12 | 1.10 | 1.07 | 1.04 | 1.01 | 0.97 | 0.94 | 0.90 | 0.86 | 0.82 | 0.78 |
| | 175 | 1.17 | 1.15 | 1.13 | 1.10 | 1.07 | 1.04 | 1.01 | 0.98 | 0.94 | 0.91 | 0.87 | 0.82 | 0.78 |
| | 200 | 1.18 | 1.16 | 1.13 | 1.11 | 1.08 | 1.05 | 1.02 | 0.98 | 0.94 | 0.91 | 0.87 | 0.82 | 0.78 |
| | 225 | 1.18 | 1.16 | 1.14 | 1.11 | 1.08 | 1.05 | 1.02 | 0.98 | 0.95 | 0.91 | 0.87 | 0.82 | 0.78 |
| | 250 | 1.19 | 1.16 | 1.14 | 1.11 | 1.08 | 1.05 | 1.02 | 0.98 | 0.95 | 0.91 | 0.87 | 0.82 | 0.78 |
| | 275 | 1.19 | 1.17 | 1.14 | 1.11 | 1.08 | 1.05 | 1.02 | 0.98 | 0.95 | 0.91 | 0.87 | 0.82 | 0.78 |
| | 300 | 1.19 | 1.17 | 1.14 | 1.11 | 1.09 | 1.05 | 1.02 | 0.99 | 0.95 | 0.91 | 0.87 | 0.82 | 0.78 |
| | 325 | 1.19 | 1.17 | 1.14 | 1.12 | 1.09 | 1.05 | 1.02 | 0.99 | 0.95 | 0.91 | 0.87 | 0.82 | 0.78 |
| | 350 | 1.19 | 1.17 | 1.14 | 1.12 | 1.09 | 1.06 | 1.02 | 0.99 | 0.95 | 0.91 | 0.87 | 0.82 | 0.78 |
| | 375 | 1.19 | 1.17 | 1.14 | 1.12 | 1.09 | 1.06 | 1.02 | 0.99 | 0.95 | 0.91 | 0.87 | 0.82 | 0.78 |
| | 400 | 1.19 | 1.17 | 1.15 | 1.12 | 1.09 | 1.06 | 1.02 | 0.99 | 0.95 | 0.91 | 0.87 | 0.82 | 0.78 |
| | 425 | 1.19 | 1.17 | 1.15 | 1.12 | 1.09 | 1.06 | 1.02 | 0.99 | 0.95 | 0.91 | 0.87 | 0.82 | 0.78 |
| | 450 | 1.19 | 1.17 | 1.15 | 1.12 | 1.09 | 1.06 | 1.02 | 0.99 | 0.95 | 0.91 | 0.87 | 0.82 | 0.78 |
| | 475 | 1.20 | 1.17 | 1.15 | 1.12 | 1.09 | 1.06 | 1.02 | 0.99 | 0.95 | 0.91 | 0.87 | 0.82 | 0.78 |
| | 500 | 1.20 | 1.17 | 1.15 | 1.12 | 1.09 | 1.06 | 1.02 | 0.99 | 0.95 | 0.91 | 0.87 | 0.82 | 0.78 |
| | 525 | 1.20 | 1.17 | 1.15 | 1.12 | 1.09 | 1.06 | 1.02 | 0.99 | 0.95 | 0.91 | 0.87 | 0.82 | 0.78 |
| | 550 | 1.20 | 1.17 | 1.15 | 1.12 | 1.09 | 1.06 | 1.02 | 0.99 | 0.95 | 0.91 | 0.87 | 0.82 | 0.78 |
| | 575 | 1.20 | 1.17 | 1.15 | 1.12 | 1.09 | 1.06 | 1.02 | 0.99 | 0.95 | 0.91 | 0.87 | 0.82 | 0.78 |
| | 600 | 1.20 | 1.17 | 1.15 | 1.12 | 1.09 | 1.06 | 1.02 | 0.99 | 0.95 | 0.91 | 0.87 | 0.82 | 0.78 |

The factor $x_3$ (in either Table 3A or 3B) is then utilized in Equation 7 as part of step 716 to obtain a third analyte concentration $G_3$.

$$G_3 = \left[ \frac{I_E - P1}{P2 * x_3} \right] \quad \text{Equation (7)}$$

where $G_3$ represents a first analyte concentration;

$I_E$ represents a total output signal (e.g., current) from the biosensor measured at one of the plurality of predetermined time positions $T_1, T_2, T_3, \ldots T_N$~test sequence interval (where $T_1$~1.0 sec., $T_2$~1.01 sec., $T_3$~1.02 secs);

P1 represents an intercept parameter of the biosensor;

P2 represents a slope parameter of the biosensor; and x₃ represents a third biosensor parametric factor based on the physical characteristic of the sample and a first analyte concentration $G_1$.

In Equation 7, for the particular embodiments described herein, P1 is about 475 nanoamps and P2 is about 9.5 nanoamps/(mg/dL).

By virtue of the description provided herein, a method of obtaining accurate analyte concentration has been attained by applicants. The method can be achieved by: applying a signal to the sample to determine a physical characteristic of the sample at step 606; driving another signal to the sample to cause a physical transformation of the sample; measuring at least one output signal from the sample at step 604; obtaining an estimated analyte concentration ($G_{EST}$) from the at least one output signal ($I_E$) at one of a plurality of predetermined time positions ($T_{PRED}$) being at least one of $T_1, T_2, T_3 \ldots T_N$) from the start of the test sequence and at least one predetermined parameter of the biosensor (P1 or P2) at step 614; generating a first parametric factor ($x_1$) of the biosensor based on the physical characteristic (IC) of the sample at step 608; calculating at step 610 a first analyte concentration based on the first parametric factor ($x_1$) of the biosensor and at least one output signal ($I_E$) measured at one of the plurality of predetermined time positions ($T_{PRED}$) from the start of the test sequence; generating a second parametric factor ($x_2$) of the biosensor based on the estimated analyte concentration ($G_{EST}$) and the physical characteristic (IC) of the sample (95) at step 616; calculating a second analyte concentration ($G_2$) based on the second parametric factor ($x_2$) of the biosensor and at least one output signal ($I_E$) measured at one of the plurality of predetermined time positions ($T_{PRED}$) from the start of the test sequence at step 618; generating a third parametric factor ($x_3$) of the biosensor based on the first analyte concentration ($G_1$) and the physical characteristic IC at step 622; calculating a third analyte concentration ($G_3$) based on the third parametric factor of the biosensor ($x_3$) and at least one output signal ($I_E$) measured at one of the plurality of predetermined time positions ($T_{PRED}$) from the start of the test sequence at step 624; and annunciating at least one of the first, second, and third analyte concentrations ($G_1$, $G_2$, $G_3$) at step 626.

FIG. 7 illustrates a variation of the second technique (modules 602, 604, 606, 614, 616, 618 and 620 in FIG. 6). In this technique, it is assumed that the user has turned on the biosensor (e.g., inserting the strip into the port connector of the meter). At step 702, a sample is deposited onto the biosensor while a voltage is applied (FIG. 4A). As the sample wets the electrodes, an output signal is generated from a working electrode (FIG. 4B). Once the output signal rises above zero, the system assumes that a test is in progress and initiates the test sequence at step 704. It is noted that during the application of the sample, before or after initiation of test sequence, the system may apply a signal AC to the sample to measure or estimate the physical characteristic of the sample at step 706. At step 708, a timer can be started at about the same time as step 704 to ensure that output signals from the working electrodes are sampled at the appropriate time positions during the test interval T. At step 710, another signal can be driven into the sample to measure output signals from the working electrodes (e.g., output signal in the form of nanoamperes). An estimated analyte concentration is derived at step 712 by measuring the output signal(s) at the appropriate time positions from one of the time positions in the test interval T in conjunction with Equation 6.1. In the preferred embodiment, the time position for deriving the estimated analyte concentration is a time point of about 2.5 seconds or about 5 seconds and any suitable time interval overlapping each of these time points may be used and the values for P1 (i.e., intercept) is about 792 nanoamps and P2 (i.e., slope) is about 10.08nA/(mg/dL) in Equation 6.1. At step 714, both the physical characteristic IC and the estimated analyte concentration can be used by the system to determine a new biosensor parameter for the biosensor $P2_{NEW}$. This parameter $P2_{NEW}$ can be generated by regression analysis of the biosensor, as noted earlier and obtained by curve fitting, a matrix or a look-up table. For reduction in computational load on the processor 300, a look-up table such as Table 4 may be utilized.

TABLE 4

Biosensor Parameter $P2_{NEW}$ based on Physical Characteristics IC and $G_{EST}$

| Glucose Estimate ($G_{EST}$) [mg/dL] | IC~Estimated Haematocrit [%] | | | | | | | |
|---|---|---|---|---|---|---|---|---|
| | 25 | 30 | 35 | 40 | 45 | 50 | 55 | 60 |
| 25 | 0.105 | 0.105 | 0.105 | 0.105 | 0.105 | 0.105 | 0.105 | 0.105 |
| 50 | 0.105 | 0.105 | 0.105 | 0.105 | 0.105 | 0.105 | 0.105 | 0.105 |
| 100 | 0.12 | 0.115 | 0.110 | 0.105 | 0.100 | 0.095 | 0.09 | 0.085 |
| 150 | 0.12 | 0.115 | 0.110 | 0.105 | 0.100 | 0.095 | 0.09 | 0.085 |
| 200 | 0.12 | 0.115 | 0.110 | 0.105 | 0.100 | 0.095 | 0.09 | 0.085 |
| 250 | 0.12 | 0.115 | 0.110 | 0.105 | 0.100 | 0.095 | 0.09 | 0.085 |
| 300 | 0.12 | 0.115 | 0.110 | 0.105 | 0.100 | 0.095 | 0.09 | 0.085 |
| 350 | 0.12 | 0.115 | 0.110 | 0.105 | 0.100 | 0.095 | 0.09 | 0.085 |
| 400 | 0.12 | 0.115 | 0.110 | 0.105 | 0.100 | 0.095 | 0.09 | 0.085 |
| 450 | 0.12 | 0.115 | 0.110 | 0.105 | 0.100 | 0.095 | 0.09 | 0.085 |
| 500 | 0.12 | 0.115 | 0.110 | 0.105 | 0.100 | 0.095 | 0.09 | 0.085 |
| 550 | 0.12 | 0.115 | 0.110 | 0.105 | 0.100 | 0.095 | 0.09 | 0.085 |
| 600 | 0.12 | 0.115 | 0.110 | 0.105 | 0.100 | 0.095 | 0.09 | 0.085 |

Once the system has obtained the new biosensor parameter or $P2_{New}$, a calculation can be made for the analyte concentration $G_{2A}$ using this parameter $P2_{New}$, as utilized with Equation 7:

$$G_{2A} = \left[\frac{I_E - P1}{P2_{NEW}}\right] \quad \text{Equation (7)}$$

where $G_{2A}$ represents a second analyte concentration;
$I_E$ represents a total output signal (e.g., current) from the biosensor measured at one of the plurality of predetermined time positions;
P1 represents an intercept parameter of the biosensor;
$P2_{NEW}$ represents a slope parameter of the biosensor based on estimated analyte concentration $G_{EST}$ and physical characteristic IC
where:

$$G_{EST} = \left[\frac{I_E - P1}{P2}\right] \quad \text{Equation (7.1)}$$

$I_E$ represents a total output signal (e.g., current) from the biosensor measured at one or another of the plurality of predetermined time positions;
P1 represents an intercept parameter of the biosensor and
P2 represents a slope parameter of the biosensor.

In the particular embodiments described herein, P1 for Equation 7 is about 400 nanoamps; the signal $I_E$ is measured at about 5 seconds; P1 for Equation 7.1 is about 792 nanoamps; P2 for Equation 7.1 is about 10.1 nA/(mg/dL) and the signal $I_E$ is measured or sampled at about 2.5 seconds for Equation 7.1.

It is noted that with respect to the new techniques described earlier, instead of the estimate of the analyte concentration in the Tables 2-3, a measured signal at the predetermined time (e.g., about 2.5 seconds or 5 seconds) could be used. This is due to the fact that the analyte estimate in these Tables are the results of the measured signals and as such, when the estimate is made by multiplying and dividing with the biosensor parametric factors P1 and P2. As such, the measured signal can be used with its raw value in the Tables instead of additional mathematical manipulations with factors P1 and P2 for the estimate in such Tables.

To verify the improvements obtained by the inventors, tests were conducted for multiple lots of 10 strips for a total of 13234 strips for the biosensor with the known technique as compared to our inventive first through third techniques. The results are summarized here in Table 5.

The results from the experiments were plotted and shown here as FIGS. 8-11. FIG. 8A illustrates graphically how those glucose results under 100 mg/dL in the known technique is biased outside of the upper boundary of 15 mg/dL below 35% hematocrit and biased below the lower boundary of −15 mg/dL at higher hematocrits above 45%. FIG. 8B illustrates graphically how those glucose results at or above 100 mg/dL in the known technique is biased outside of the upper boundary of 15% below 35% hematocrit and biased below the lower boundary of −15% for higher hematocrits above 45%.

In contrast, when the first technique is utilized for the same sample set, the results indicate that for analyte concentration below 100 mg/dL, the results using the first technique (FIG. 9A) were much better than the known technique (FIG. 8A). Similarly for analyte concentration at or greater than 100 mg/dL, the results of the first technique (FIG. 9B) were also better than the known technique (FIG. 8B).

For the second technique (FIGS. 10A and 10B) as compared to the known technique (FIGS. 8A and 8B), the results

TABLE 5

Results per lot

| | Known Technique % of samples within | | First Technique - $G_1$ % of samples within | | Second Technique - $G_2$ % of samples within | | Third Technique - $G_3$ % of samples within | |
|---|---|---|---|---|---|---|---|---|
| Lot | <100 mg/dL ± 15 mg/dL | ≥100 mg/dL ± 15% | <100 mg/dL ± 15 mg/dL | ≥100 mg/dL ± 15% | <100 mg/dL ± 15 mg/dL | ≥100 mg/dL ± 15% | <100 mg/dL ± 15 mg/dL | ≥100 mg/dL ± 15% |
| 1 | 100 | 61.4 | 100 | 87.4 | 99.6 | 94.9 | 100 | 94.7 |
| 2 | 98.5 | 59.7 | 98.9 | 77.5 | 98.9 | 92.6 | 98.9 | 92.3 |
| 3 | 99.2 | 72.6 | 99.5 | 89.8 | 100 | 98.1 | 99.7 | 98.3 |
| 4 | 99.7 | 67.5 | 99.3 | 84.3 | 99 | 98.2 | 99.5 | 98.2 |
| 5 | 90 | 64 | 97.2 | 87.8 | 99 | 95.6 | 98.9 | 95.5 |
| 6 | 87.9 | 68.4 | 96.5 | 94.3 | 99.1 | 91.9 | 99.2 | 91.8 |
| 7 | 89 | 69.8 | 93.7 | 92.5 | 98.8 | 86.8 | 99 | 86.7 |
| 8 | 92.7 | 58.4 | 97.8 | 83.4 | 96.5 | 95.9 | 96.3 | 95.8 |
| 9 | 91 | 63.7 | 99.1 | 85.8 | 98.4 | 96 | 99.1 | 95.9 |
| 10 | 93.9 | 66.5 | 98.9 | 91.6 | 99.8 | 98.8 | 99.8 | 98.9 |
| 11 | 82.3 | 61.8 | 94.7 | 94.8 | 99.2 | 95.5 | 99.2 | 95.1 |
| 12 | 90 | 69.4 | 96 | 86.7 | 95.3 | 96.7 | 95.3 | 97 |
| 13 | 87.4 | 66.1 | 97 | 87 | 97 | 96.1 | 97 | 96.4 |
| 14 | 82.9 | 61.8 | 95 | 93.2 | 98.3 | 97 | 98.3 | 96.8 |

It is noted that the quantification of the improvement can be shown by the "bias" at different levels of hematocrit. The bias, which is an estimate of the relative error in the glucose measurement, was calculated for each glucose concentration determined with the method described in this example. The bias for each glucose concentration was determined with equations of the form:

$$Bias_{abs} = G_{calculated} - G_{reference}$$

for $G_{reference}$ less than 100 mg/dL glucose and $$Bias\ \% = \frac{G_{calculated} - G_{reference}}{G_{reference}}$$

for $G_{reference}$ greater than or equal to 100 mg/dL glucose where
$Bias_{abs}$ is absolute bias,
$Bias_\%$ is percent bias,
$G_{calculated}$ is the glucose concentration determined by the method herein and
$G_{reference}$ is the reference glucose concentration.

are just as impressive as or even better than the known technique (or the first technique) when the centroids of the data are compared across the figures.

For the third technique (FIGS. 11A and 11B), it is noted here that there is no significant difference between the second and third techniques (see Table 5), however this is largely given by the size of the correction Tables 1&2. If a finer resolution of "bins" for glucose and haematocrit was used, an improvement in the results for the third technique is believed to be obtainable.

As can be seen in the second or third technique, for glucose concentration less than 100 mg/dL, at least 95% of the final analyte concentration values of the batch of test strips are within ±15 mg/dL of the referential analyte concentration.

It should be noted that the step of applying the first signal and the driving of the second signal is in sequential order in that the order may be the first signal then the second signal or both signals overlapping in sequence; alternatively, the second signal first then the first signal or both signals overlapping in sequence. Alternatively, the applying of the first signal and the driving of the second signal may take place simultaneously.

It is noted that in the preferred embodiments, the measurement of a signal output for the glucose concentration is performed prior to the estimation of the physical characteristic (e.g., hematocrit). Alternatively, the physical characteristic (e.g., hematocrit) level can be estimated, measured, or obtained prior to the measurement of the glucose concentration.

Although the method may specify only one sampling time point, the method may include sampling as many time points as required, such as, for example, sampling the signal output continuously (e.g., at specified sampling time such as, every one millisecond to 100 milliseconds) from the start of the test sequence until at least about 10 seconds after the start and the results stored for processing near the end of the test sequence. Applicants note that the appropriate sampling time is measured from the start of the test sequence but any appropriate datum may be utilized in order to determine when to sample the output signal. As a practical matter, the system can be programmed to sample the output signal at an appropriate time sampling interval during the entire test sequence such as for example, one sampling every 100 milliseconds or even as little as about 1 milliseconds. In this variation, the sampled signal output at the specified sampling time point T is the value used to calculate the analyte concentration.

The measuring time positions $T_1$, $T_2$, $T_3$ . . . $T_N$ at which the system is sampling the output signal of the biosensor are based on both the qualitative category of the estimated analyte and measured or estimated physical characteristic and is predetermined based on regression analysis of a large sample size of actual physiological fluid samples. Applicants note that the appropriate sampling time is measured from the start of the test sequence but any appropriate datum may be utilized in order to determine when to sample the output signal. As a practical matter, the system can be programmed to sample the output signal at an appropriate time sampling interval during the entire test sequence such as for example, one sampling every 100 milliseconds or even as little as about 1 milliseconds. By sampling the entire signal output transient during the test sequence, the system can perform all of the needed calculations near the end of the test sequence rather than attempting to synchronize the sampling time with the set time point, which may introduce timing errors due to system delay.

By virtue of the descriptions and teachings provided herein, applicant was able to devise a glucose test strip that has a substrate, a plurality of electrodes disposed on the substrate and connected to respective electrode connectors. The test strip 100 includes at least a reagent disposed on at least one of the plurality of electrodes, in which at least one of the electrodes is configured to sense a physical characteristic of fluid sample deposited on the at least one electrode and at least another of the electrodes is configured to measure output signal from the sample upon application of input signal to the sample. Included with the test strip are instructions for use with a glucose meter. The instructions includes indicia embedded in an appropriate communication medium (e.g., paper, computer, internet, audio or visual medium or the like) to a user to inset the electrode connectors of the test strip to a test strip port of the glucose meter. The meter indicated for use with the glucose test strip includes a test strip port connector configured to connect to respective electrode connectors of a test strip, and a microprocessor in electrical communication with the test strip port connector to apply electrical signals or sense electrical signals from a plurality of electrodes of the test strip connected to the respective electrode connectors of the test strip during a test sequence. The instructions further include indicia embedded in an appropriate communication medium (e.g., paper, computer, internet, audio or visual medium or the like) to the user to deposit a fluid sample proximate at least one of the plurality of electrodes so that the microprocessor 300 is operable to: (a) start an analyte test sequence upon deposition of a sample; (b) apply a signal to the sample to determine a physical characteristic of the sample; (c) drive another signal to the sample; (d) measure at least one output signal from at least one of the electrodes; (e) derive an estimated analyte concentration from the at least one output signal at one of a plurality of predetermined time positions from the start of the test sequence; (f) obtain a new parameter of the biosensor based on the estimated analyte concentration and the physical characteristic of the sample; (g) calculate an analyte concentration based on the new parameter of the biosensor and a output signal measured at the one or another of the plurality of predetermined time positions from the start of the test sequence; and (h) annunciate the analyte concentration.

Although the techniques described herein have been directed to determination of glucose, the techniques can also applied to other analytes (with appropriate modifications by those skilled in the art) that are affected by physical characteristic(s) of the fluid sample in which the analyte(s) is disposed in the fluid sample. For example, the physical characteristic (e.g., hematocrit, viscosity or density and the like) of a physiological fluid sample could be accounted for in determination of ketone or cholesterol in the fluid sample, which may be physiological fluid, calibration, or control fluid. Other biosensor configurations can also be utilized. For example, the biosensors shown and described in the following U.S. patents can be utilized with the various embodiments described herein: U.S. Pat. Nos. 6,179,979; 6,193,873; 6,284,125; 6,413,410; 6,475,372; 6,716,577; 6,749,887; 6,863,801; 6,890,421; 7,045,046; 7,291,256; 7,498,132, all of which are incorporated by reference in their entireties herein.

As is known, the detection of the physical characteristic does not have to be done by alternating signals but can be done with other techniques. For example, a suitable sensor can be utilized (e.g., US Patent Application Publication No. 20100005865 or EP1804048 B1) to determine the viscosity or other physical characteristics. Alternatively, the viscosity can be determined and used to derive for hematocrits based on the known relationship between hematocrits and viscosity as described in "Blood Rheology and Hemodynamics" by Oguz K. Baskurt, M.D., Ph.D., 1 and Herbert J. Meiselman, Sc.D., *Seminars in Thrombosis and Hemostasis*, volume 29, number 5, 2003.

As described earlier, the microcontroller or an equivalent microprocessor (and associated components that allow the microcontroller to function for its intended purpose in the intended environment such as, for example, the processor 300 in FIG. 2B) can be utilized with computer codes or software instructions to carry out the methods and techniques described herein. Applicants note that the exemplary microcontroller 300 (along with suitable components for functional operation of the processor 300) in FIG. 2B is embedded with firmware or loaded with computer software representative of the logic diagrams in FIGS. 6 and 7 and the microcontroller 300, along with associated connector 220 and interface 306 and equivalents thereof, are the means for:

(a) applying first and second input signals to a sample deposited on the biosensor during a test sequence;

(b) measuring a physical characteristic of the sample from output signals of one of the first and second input signals;

(c) deriving an estimated a glucose concentration at one of a plurality of predetermined time points from the start of the test sequence based on the other of the first and second input signals;

(d) generating a new parameter of the biosensor based on the physical characteristic and the estimated glucose concentration; and (e) calculating a glucose concentration based on the new parameter of the biosensor and a signal output at one or another of the plurality of predetermined time positions.

In particular, it is noted that the means (and their hardware or software equivalents) for performing functions (a)-(e) include modules 602, 604, 606, 608, and 610 for the first technique; modules 602, 604, 606, 614, 616, and 618 for the second technique; and modules 602, 604, 606, 608, 610, 622, and 624 for the third technique.

In general, hand-held test meters for use with an analytical test strip in the determination of an analyte (such as glucose) in a bodily fluid sample (i.e., a whole blood sample) according to embodiments of the present disclosure include a housing, a microcontroller block disposed in the housing, and a phase-shift-based hematocrit measurement block (also referred to as a phase-shift-based hematocrit circuit). In such hand-held test meters, the phase-shift-based hematocrit measurement block includes a signal generation sub-block, a low pass filter sub-block, an analytical test strip sample cell interface sub-block, a transimpedance amplifier sub-block, and a phase detector sub-block. In addition, the phase-shift-based hematocrit measurement block and microcontroller block are configured to measure the phase shift of a bodily fluid sample in a sample cell of an analytical test strip inserted in the hand-held test meter and the microcontroller block is also configured to compute the hematocrit of the bodily fluid sample based on the measured phase shift.

Hand-held test meters according to embodiments of the present disclosure are beneficial in that they provide improved accuracy of analyte determination (such as glucose determination) in whole blood samples by measuring the hematocrit of the whole blood sample and then employing the measured hematocrit during analyte determination.

One example of a hand-held test meter that can be readily modified as a hand-hand test meter according to the present disclosure is the commercially available OneTouch® Ultra® 2 glucose meter from LifeScan Inc. (Milpitas, Calif.). Additional examples of hand-held test meters that can also be modified are found in U.S. Patent Application Publications No's. 2007/0084734 (published on Apr. 19, 2007) and 2007/0087397 (published on Apr. 19, 2007) and in International Publication Number WO2010/049669 (published on May 6, 2010), each of which is hereby incorporated herein in full by reference.

Figure 12:
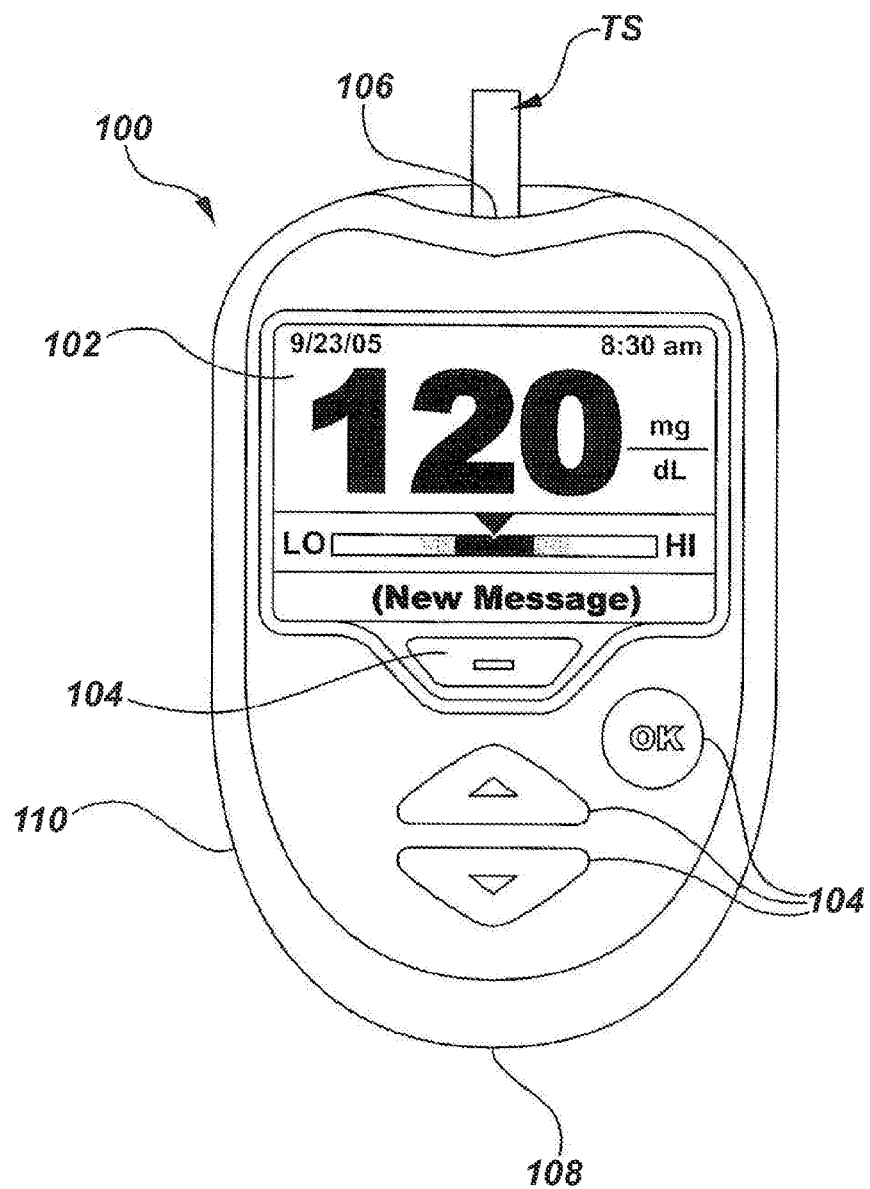
FIG. 12 is a simplified depiction of a hand-held test meter according to an embodiment of the present disclosure.
Figure 13:
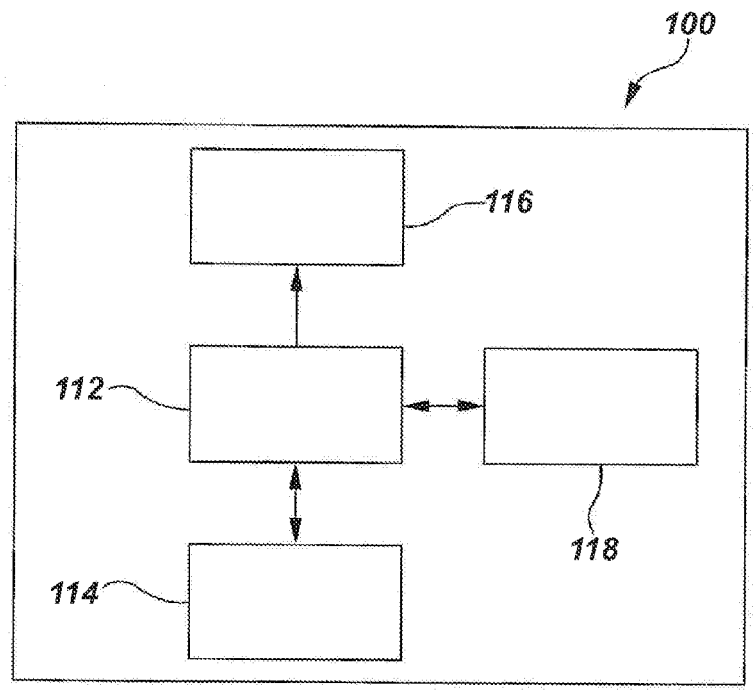
FIG. 13 is a simplified block diagram of various blocks of the hand-held test meter of FIG. 12.
Figure 14:
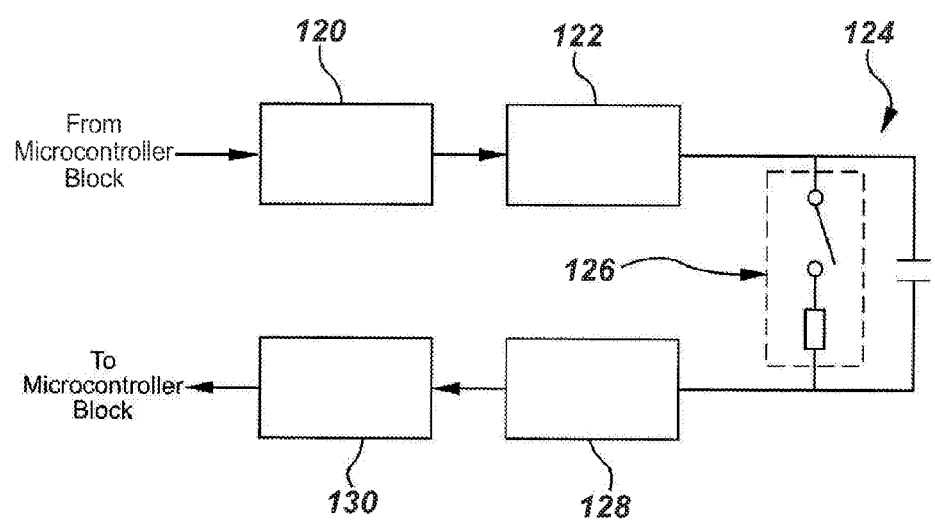
FIG. 14 is a simplified block diagram of a phase-shift-based hematocrit measurement block as can be employed in embodiments according to the present disclosure.
Figure 15:
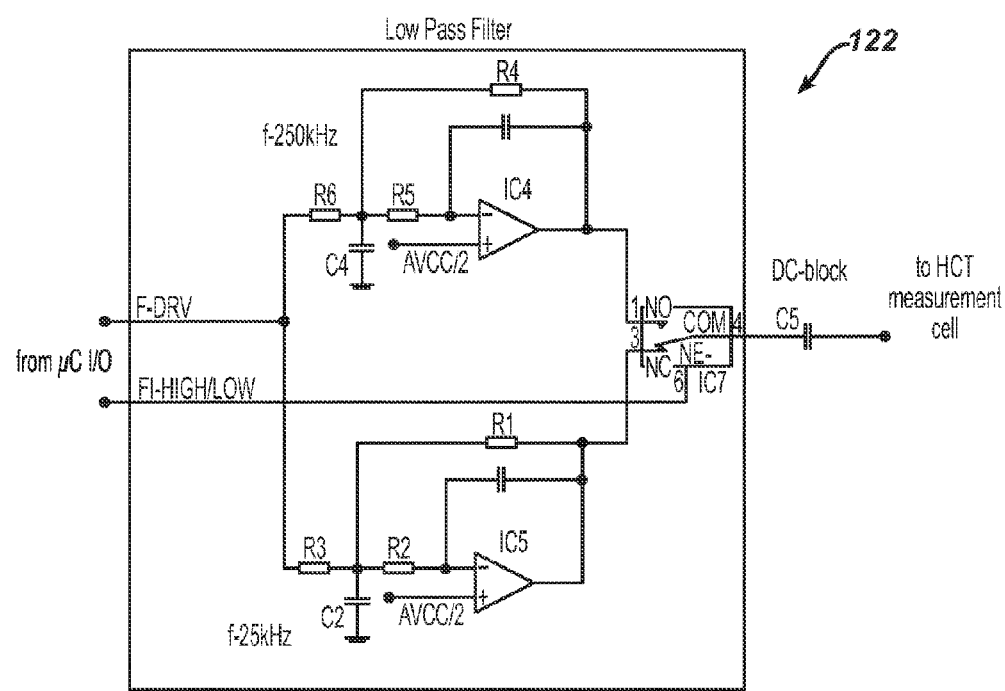
FIG. 15 is a simplified annotated schematic diagram of a dual low pass filter sub-block as can be employed in embodiments of the present disclosure.
Figure 16:
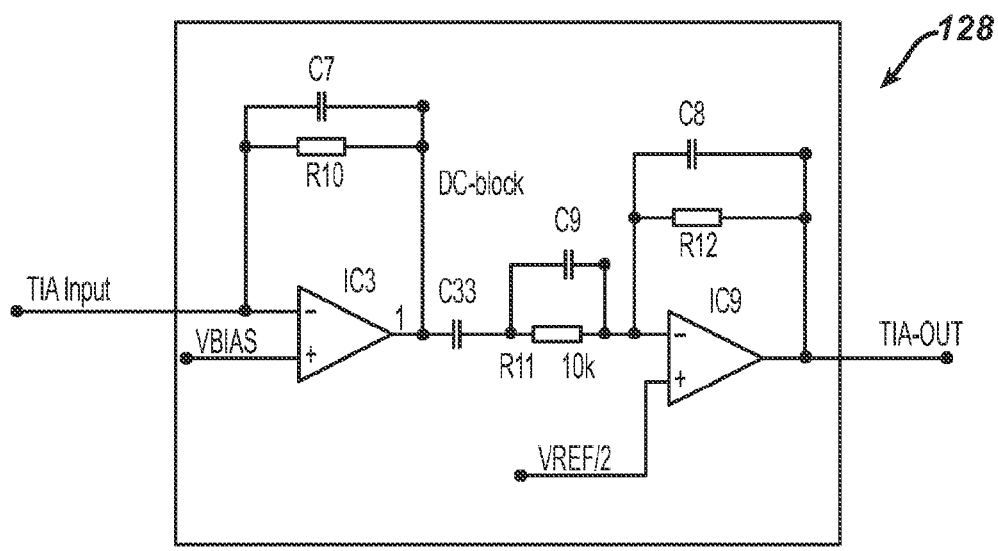
FIG. 16 is a simplified annotated schematic diagram of a transimpedance amplifier (TIA) sub-block as can be employed in embodiments of the present disclosure.
Figure 17:
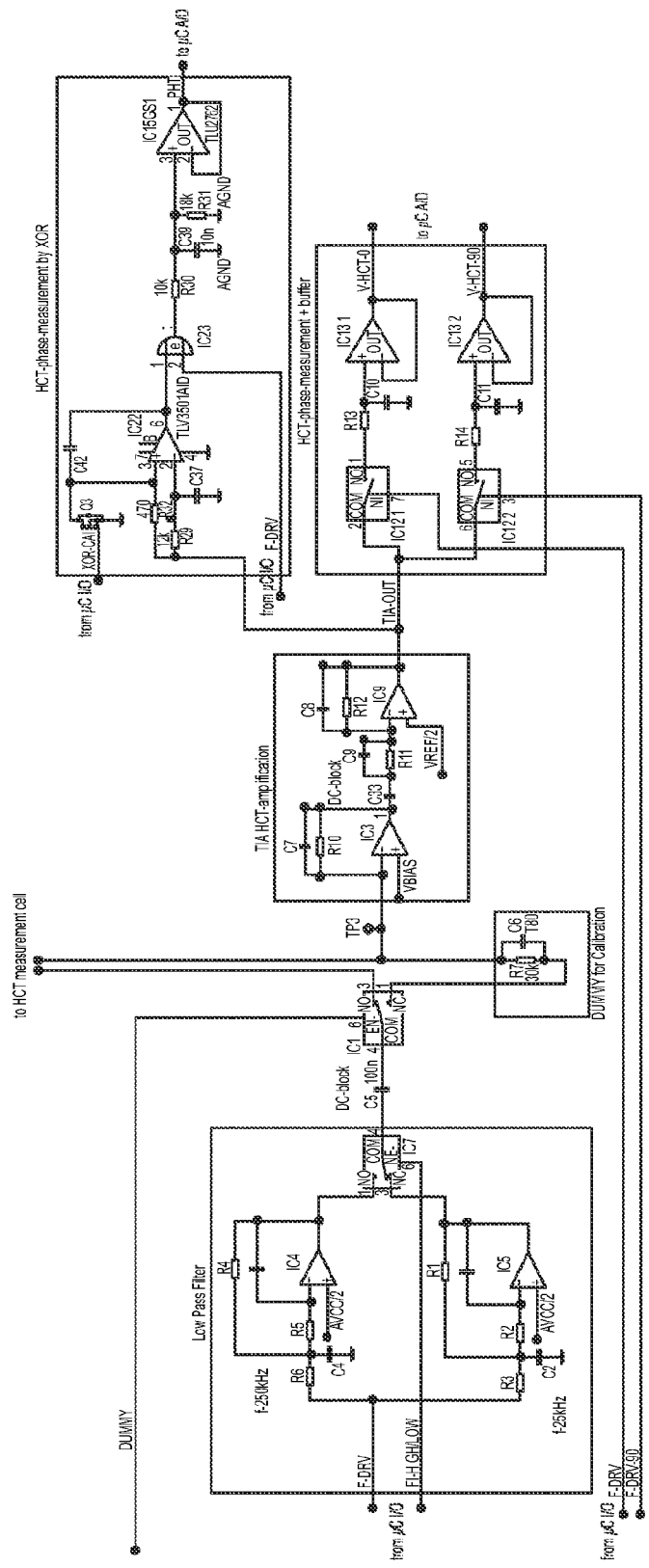
FIG. 17 is a simplified annotated schematic block diagram depicting a dual low pass filter sub-block, a calibration load sub-block, an analytical test strip sample cell interface sub-block, a transimpedance amplifier sub-block, an XOR phase shift measurement sub-block and a Quadratur DEMUX phase-shift measurement sub-block as can be employed in a phase-shift-based hematocrit measurement block of embodiments of the present disclosure.

FIG. 12 is a simplified depiction of a hand-held test meter 100 according to an embodiment of the present disclosure. FIG. 13 is a simplified block diagram of various blocks of hand-held test meter 100. FIG. 14 is a simplified combined block diagram of a phase-shift-based hematocrit measurement block of hand-held test meter 100. FIG. 15 is a simplified annotated schematic diagram of a dual low pass filter sub-block of hand-held test meter 100. FIG. 16 is a simplified annotated schematic diagram of a transimpedance amplifier sub-block of hand-held test meter 100. FIG. 17 is a simplified annotated schematic block diagram of portions of a phase-shift-based hematocrit measurement block of hand-held test meter 100.

Referring to FIGS. 12 through 17, hand-held test meter 100 includes a display 102, a plurality of user interface buttons 104, a strip port connector 106, a USB interface 108, and a housing 110 (see FIG. 12). Referring to FIG. 13 in particular, hand-held test meter 100 also includes a microcontroller block 112, a phase-shift-based hematocrit measurement block 114, a display control block 116, a memory block 118 and other electronic components (not shown) for applying a test voltage to analytical test strip (labeled TS in FIG. 12), and also for measuring an electrochemical response (e.g., plurality of test current values) and determining an analyte based on the electrochemical response. To simplify the current descriptions, the figures do not depict all such electronic circuitry.

Display 102 can be, for example, a liquid crystal display or a bi-stable display configured to show a screen image. An example of a screen image may include a glucose concentration, a date and time, an error message, and a user interface for instructing an end user how to perform a test.

Strip port connector 106 is configured to operatively interface with an analytical test strip TS, such as an electrochemical-based analytical test strip configured for the determination of glucose in a whole blood sample. Therefore, the analytical test strip is configured for operative insertion into strip port connector 106 and to operatively interface with phase-shift-based hematocrit measurement block 114 via, for example, suitable electrical contacts.

USB Interface 108 can be any suitable interface known to one skilled in the art. USB Interface 108 is essentially a passive component that is configured to power and provide a data line to hand-held test meter 100.

Once an analytical test strip is interfaced with hand-held test meter 100, or prior thereto, a bodily fluid sample (e.g., a whole blood sample) is introduced into a sample chamber of the analytical test strip. The analytical test strip can include enzymatic reagents that selectively and quantitatively transform an analyte into another predetermined chemical form. For example, the analytical test strip can include an enzymatic reagent with ferricyanide and glucose oxidase so that glucose can be physically transformed into an oxidized form.

Memory block 118 of hand-held test meter 100 includes a suitable algorithm and can be configured, along with microcontroller block 112 to determine an analyte based on the electrochemical response of analytical test strip and the hematocrit of the introduced sample. For example, in the determination of the analyte blood glucose, the hematocrit can be used to compensate for the effect of hematocrit on electrochemically determined blood glucose concentrations.

Microcontroller block 112 is disposed within housing 110 and can include any suitable microcontroller and/or microprocessor known to those of skill in the art. One such suitable microcontroller is a microcontroller commercially available from Texas Instruments, Dallas, Tex. USA and part number MSP430F5138. This microcontroller can generate a square wave of 25 to 250 kHz and a 90 degree phase-shifted wave of the same frequency and, thereby, function as a signal generation s-block described further below. MSP430F5138 also has Analog-to-Digital (A/D) processing capabilities suitable for measuring voltages generated by phase shift based hematocrit measurement blocks employed in embodiments of the present disclosure.

Referring in particular to FIG. 14, phase-shift-based hematocrit measurement block 114 includes a signal generation sub-block 120, a low pass filter sub-block 122, an analytical test strip sample cell interface sub-block 124, an optional calibration load block 126 (within the dashed lines of FIG. 14), a transimpedance amplifier sub-block 128, and a phase detector sub-block 130.

As described further below, phase-shift-based hematocrit measurement block 114 and microcontroller block 112 are configured to measure the phase shift of a bodily fluid sample in a sample cell of an analytical test strip inserted in the hand-held test meter by, for example, measuring the phase shift of one or more high frequency electrical signals driven through the bodily fluid sample. In addition, microcontroller block 112 is configured to compute the hematocrit of the bodily fluid based on the measured phase shift. Microcontroller 112 can compute the hematocrit by, for example, employing an A/D converter to measure voltages received from a phase-detector sub-block, convert the voltages into a phase-shift and then employing a suitable algorithm or look-up table to convert the phase-shift into a hematocrit value. Once apprised of the present disclosure, one skilled in the art will recognize that such an algorithm and/or look-up table will be configured to take into account various factors such as strip geometry (including electrode area and sample chamber volume) and signal frequency.

It has been determined that a relationship exists between the reactance of a whole blood sample and the hematocrit of that sample. Electrical modeling of a bodily fluid sample (i.e., a whole blood sample) as parallel capacitive and resistive components indicates that when an alternating current (AC) signal is forced through the bodily fluid sample, the phase shift of the AC signal will be dependent on both the frequency of the AC voltage and the hematocrit of the sample. Moreover, modeling indicates that hematocrit has a relatively minor effect on the phase shift when the frequency of the signal is in the range of approximately 10 kHz to 25 kHz and a maximum effect on the phase shift when the frequency of the signal is in the range of approximately 250 kHz to 500 KHz. Therefore, the hematocrit of a bodily fluid sample can be measured by, for example, driving AC signals of known frequency through the bodily fluid sample and detecting their phase shift. For example, the phase-shift of a signal with a frequency in the range of 10 kHz to 25 kHz can be used as a reference reading in such a hematocrit measurement while the phase shift of a signal with a frequency in the range of 250 kHz to 500 kHz can be used as the primary measurement.

Referring to FIGS. 14 through 17 in particular, signal generation sub-block 120 can be any suitable signal generation block and is configured to generate a square wave (0V to Vref) of a desired frequency. Such a signal generation sub-block can, if desired, be integrated into microcontroller block 112.

The signal generated by signal generation sub-block 120 is communicated to dual low pass filter sub-block 122, which is configured to convert the square wave signal to a sine wave signal of a predetermined frequency. The dual LPF of FIG. 15 is configured to provide both a signal of a first frequency (such as a frequency in the range of 10 kHz to 25 kHz) and a signal of a second frequency (such as a frequency in the range of 250 kHz to 500 kHz) to the analytical test strip sample cell interface sub-block and an analytical test strips' sample chamber (also referred to as the HCT measurement cell). Selection of the first and second frequency is accomplished using switch IC7 of FIG. 15. The dual LPF of FIG. 15 includes employs two suitable operational amplifiers (IC4 and IC5) such as the operational amplifier available from Texas Instruments, Dallas, Tex., USA as high-speed, voltage feedback, CMOS operational amplifier part number OPA354.

Referring to FIG. 15, F-DRV represents a square wave input of either a low or high frequency (e.g., 25 kHz or 250 kHz) and is connected to both IC4 and IC5. Signal Fi-HIGH/LOW (from the microcontroller) selects the output of dual low pass filter sub-block 122 via switch IC7. C5 in FIG. 15 is configured to block the operating voltage of dual low pass filter sub-block 122 from the HCT measurement cell.

Although a specific dual LPF is depicted in FIG. 15, dual low pass filter sub-block 122 can be any suitable low pass filter sub-block known to one skilled in the art including, for example, any suitable multiple feedback low pass filter, or a Sallen and Key low pass filter.

The sine wave produced by low pass filter sub-block 122 is communicated to analytical test strip sample cell interface sub-block 124 where it is driven across the sample cell of the analytical test strip (also referred to as an HCT measurement cell). Analytical test strip sample cell interface block 124 can be any suitable sample cell interface block including, for example, an interface block configured to operatively interface with the sample cell of the analytical test strip via first electrode and second electrodes of the analytical test strip disposed in the sample cell. In such a configuration, the signal can be driven into the sample cell (from the low pass filter sub-block) via the first electrode and picked-up from the sample cell (by the transimpedance amplifier sub-block) via the second electrode as depicted in FIG. 17.

The current produced by driving the signal across the sample cell is picked-up by transimpedance amplifier sub-block 128 and converted into a voltage signal for communication to phase detector sub-block 130.

Transimpedance sub-block 128 can be any suitable transimpedance sub-block known to one skilled in the art. FIG. 16 is a simplified annotated schematic block diagram of one such transimpedance amplifier sub-block (based on two OPA354 operational amplifiers, IC3 and IC9). The first stage of TIA sub-block 128 operates at, for example, 400 mV, which limits the AC amplitude to +/−400 mV. The second stage of TIA sub-block 128 operates at Vref/2, a configuration which enables the generation of an output of the full span of the microcontroller A/D inputs. C9 of TIA sub-block 128 serves as a blocking component that only allows an AC sine wave signal to pass.

Phase detector sub-block 130 can be any suitable phase detector sub-block that produces either a digital frequency that can be read back by microcontroller block 112 using a capture function, or an analog voltage that can be read back by microcontroller block 112 using an analog to digital converter. FIG. 17 depicts a schematic that includes two such phase detector sub-blocks, namely an XOR phase detector (in the upper half of FIG. 17 and including IC22 and IC23) and a Quadrature DEMUX phase detector (in the lower half of FIG. 17 and including IC12 and IC13).

FIG. 17 also depicts a calibration load sub-block 126 that includes a switch (IC16) and a dummy load R7 and C6. Calibration load sub-block 126 is configured for the dynamic measurement of a phase offset for the known phase shift of zero degrees produced by resistor R7, thus providing a phase offset for use in calibration. C6 is configured to force a predetermined slight phase shift, e.g. to compensate for phase delays caused by parasitic capacities in the signal traces to the sample cell, or for phase delays in the electrical circuits (LPF and TIA).

The Quadrature DEMUX phase detector circuit of FIG. 17 includes two portions, one portion for a resistive part of the incoming AC signal and one portion for the reactive portion of the incoming AC signal. Use of such two portions enables the simultaneous measurement of both the resistive and reactive portion of the AC signal and a measurement range that covers 0 degrees to 360 degrees. The Quadrature DEMUX circuit of FIG. 17 generates two separate output voltages. One of these output voltages represents the "in phase measurement" and is proportional to the "resistive" part of the AC signal, the other output voltage represents the "Quadrature Measurement" and is proportional to the "reactive part of the signal. The phase shift is calculated as:

$$\Phi = \tan^{-1}(V_{QUAD\text{-}PHASE}/V_{IN\text{-}PHASE})$$

Such a Quadrature DEMUX phase detector circuit can also be employed to measure the impedance of a bodily fluid sample in the sample cell. It is hypothesized, without being bound, that the impedance could be employed along with the phase-shift, or independently thereof, to determine the hematocrit of the bodily sample. The amplitude of a signal forced through the sample cell can be calculated using the two voltage outputs of the Quadrature DEMUX circuit as follows:

$$\text{Amplitude} = \text{SQR}(V_{QUAD\text{-}PHASE})^2 + (V_{IN\text{-}PHASE})^2)$$

This amplitude can then be compared to an amplitude measured for the known resistor of calibration load block 126 to determine the impedance.

The XOR phase detector portion has a measurement range of 0° to 180°, or alternatively a measurement range of −90° to +90°, depending whether the "Square wave input from µC" is in phase to the sine wave or is set to a 90° phase shift. The XOR phase detector produces an output frequency that is always double the input frequency, however the duty cycle varies. If both inputs are perfectly in phase, the output is LOW, if both inputs are 180° shifted the output is always HIGH. By integrating the output signal (e.g. via a simple RC element) a voltage can be generated that is directly proportional to the phase shift between both inputs.

Once apprised of the present disclosure, one skilled in the art will recognize that phase detector sub-blocks employed in embodiments of the present disclosure can take any suitable form and include, for example, forms that employ rising edge capture techniques, dual edge capture techniques, XOR techniques and synchronous demodulation techniques.

Since low pass filter sub-block 122, transimpedance amplifier sub-block 128 and phase detector sub-block 130 can introduce a residual phase shift into phase-shift-based hematocrit measurement block 114, calibration load block 126 can be optionally included in the phase-shift-based hematocrit measurement block. Calibration load block 126 is configured to be essentially resistive in nature (for example a 33 k-ohm load) and, therefore, induces no phase shift between excitation voltage and generated current. Calibration load block 126 is configured to be switched in across the circuit to give a "zero" calibration reading. Once calibrated, the hand-held test meter can measure the phase shift of a bodily fluid sample, subtract the "zero" reading to compute a corrected phase shift and subsequently compute the bodily sample hematocrit based on the corrected phase shift.

Figure 18:
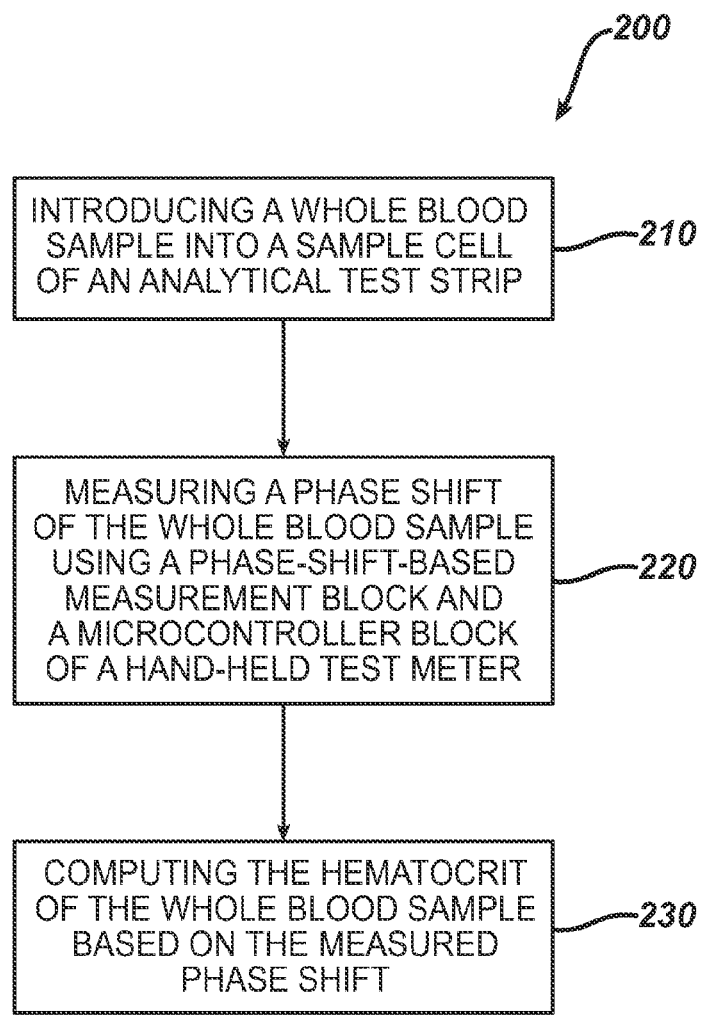
FIG. 18 is a flow diagram depicting stages in a method for employing a hand-held test meter according to an embodiment of the present disclosure.

FIG. 18 is a flow diagram depicting stages in a method 200 for employing a hand-held test meter and analytical test strip (e.g., an electrochemical-based analytical test strip). Method 200, at step 210, includes introducing a whole blood sample into a sample cell of the analytical test strip.

At step 220, a phase shift of the whole blood sample in the sample cell is measured using a phase-shift-based measurement block and a microcontroller block of a hand-held test meter. Method 200 further includes computing the hematocrit of whole blood sample based on the measured phase shift using the microcontroller block (see step 230 of FIG. 18).

Moreover, while the invention has been described in terms of particular variations and illustrative figures, those of ordinary skill in the art will recognize that the invention is not limited to the variations or figures described. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well.

The invention claimed is:

1. A method of determining an analyte concentration from a fluid sample with a biosensor having at least two electrodes and a reagent disposed on at least one of the electrodes, the method comprising:
   starting an analyte test sequence upon deposition of a sample on the biosensor;
   applying a first signal to the sample to determine a physical characteristic of the sample wherein the physical characteristic is hematocrit level;
   driving a second signal to the sample to cause a chemical transformation of the sample;
   measuring at least one output signal from the sample;
   obtaining a biosensor parametric factor from a look-up table or matrix based on the determined hematocrit level; and
   calculating an analyte concentration based on the biosensor parametric factor and the at least one output signal measured at one of a plurality of predetermined time positions from the start of the test sequence based on the relationship:

$$G_1 = \left[ \frac{I_E - P1}{P2 * x_2} \right]$$

where G1 is the analyte concentration;
   $I_E$ represents a total output signal of the electrodes of the biosensor measured at the one of the plurality of predetermined time positions;
   P1 represents a known batch intercept of the biosensor;
   P2 represents a known batch slope of the biosensor; and
   $x_1$ represents the biosensor parametric factor based on the determined hematocrit level of the sample; and
   annunciating the analyte concentration.

2. The method of claim 1, in which the applying of the first signal and the driving of the second signal may be in sequential order.

3. The method of claim 1, in which the applying of the first signal overlaps with the driving of the second signal.

4. The method of claim 1, in which the applying of the first signal comprises directing an alternating signal to the sample so that the hematocrit level of the sample may be determined from an output of the alternating signal.

5. The method of claim 4, in which the physical characteristic comprises an impedance characteristic representative of hematocrit level of the sample and the analyte comprises glucose.

6. The method of claim 5, in which the applying of the first signal comprises including a step of driving first and second alternating signals at different respective frequencies in which a first frequency may be lower than the second frequency.

7. The method of claim 6, in which the first frequency may be at least one order of magnitude lower than the second frequency.

8. The method of claim 7, in which the first frequency comprises any frequency in the range of about 10 kHz to about 250 kHz.

9. The method of claim 1, in which the one of the plurality of predetermined time positions for measuring at least one output signal during the test sequence may be about 2.5 seconds after a start of the test sequence.

10. The method of claim 9, in which the one of the plurality of predetermined time positions comprises a time interval that overlaps a time point of 2.5 seconds after the start of the test sequence.

11. The method of claim 1, in which another one of the plurality of predetermined time positions for measuring at least one output signal during the test sequence may be a time point of about 5 seconds after a start of the test sequence.

12. The method of claim 1, in which one of the plurality of predetermined time positions comprises any time point at less than five seconds from a start of the test sequence.

13. The method of claim 12, in which the another one of the plurality of predetermined time positions comprises any time point at less than ten seconds from a start of the test sequence.

14. The method of claim 13, in which the one of the plurality of predetermined time positions comprises a time interval overlapping a time point of 2.5 seconds after the start of the test sequence and the another of the plurality of predetermined time positions comprises a time interval overlapping a time point of 5 seconds after the start of the test sequence.

15. The method of claim 1, in which the at least two electrodes and at least two other electrodes are disposed in the same chamber provided on the substrate.

16. The method of claim 1, in which the at least two electrodes comprise two electrodes to measure the hematocrit level and the analyte concentration.

17. The method of claim 1, in which the at least two electrodes comprise a first set of at least two electrodes to determine the hematocrit level of the sample and a second set of at least two other electrodes to determine the analyte concentration.

18. The method of claim 17, in which all of the electrodes are disposed on a same plane defined by a substrate of the biosensor.

19. The method of claim 16, in which a third electrode may be disposed proximate the first set of at least two electrodes and connected to the second set of at least two other electrodes.

20. The system method of claim 18, in which a reagent may be disposed proximate the second set of at least two other electrodes and no reagent may be disposed on the first set of at least two electrodes.

* * * * *